(12) United States Patent
Ehrenreich et al.

(10) Patent No.: US 9,730,820 B2
(45) Date of Patent: Aug. 15, 2017

(54) STENT DELIVERY SYSTEM HAVING A FIBROUS MATRIX COVERING WITH IMPROVED STENT RETENTION

(71) Applicant: Abbott Cardiovascular Systems Inc., Santa Clara, CA (US)

(72) Inventors: Kevin J. Ehrenreich, San Francisco, CA (US); Richard Newhauser, Emerald Hills, CA (US); Randolf von Oepen, Aptos, CA (US); John J. Stankus, Campbell, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 120 days.

(21) Appl. No.: 13/947,855

(22) Filed: Jul. 22, 2013

(65) Prior Publication Data

US 2013/0310914 A1 Nov. 21, 2013
US 2017/0020703 A9 Jan. 26, 2017

Related U.S. Application Data

(60) Division of application No. 13/069,020, filed on Mar. 22, 2011, now Pat. No. 8,500,687, which is a
(Continued)

(51) Int. Cl.
*A61M 29/00* (2006.01)
*A61M 31/00* (2006.01)
(Continued)

(52) U.S. Cl.
CPC ............... *A61F 2/95* (2013.01); *A61F 2/958* (2013.01); *A61L 29/16* (2013.01);
(Continued)

(58) Field of Classification Search
CPC .... A61M 2025/1031; A61M 2025/105; A61M 2025/1075; A61M 2025/1086; A61F 2002/9583; A61F 2/958
See application file for complete search history.

(56) References Cited

U.S. PATENT DOCUMENTS 4,564,014 A 1/1986 Fogarty et al.
4,878,906 A 11/1989 Lindemann et al.
(Continued)

FOREIGN PATENT DOCUMENTS

DE 10244847 4/2004
EP 372088 6/1990
(Continued)

OTHER PUBLICATIONS

U.S. Appl. No. 12/238,627, Sep. 23, 2011 Issue Fee payment.
(Continued)

*Primary Examiner* — Rebecca E Eisenberg
(74) *Attorney, Agent, or Firm* — Baker Botts L.L.P.

(57) ABSTRACT

Stent delivery system comprising a catheter shaft having a proximal end portion and a distal end portion and an expandable member provided at the distal end portion of the shaft, the expandable member having a delivery condition and a deployed condition and formed at least in part from a matrix of fiber elements to define a continuous surface substantially free of openings when in the delivery condition.

15 Claims, 7 Drawing Sheets

Related U.S. Application Data continuation-in-part of application No. 12/238,627, filed on Sep. 26, 2008, now Pat. No. 8,076,529, and a continuation-in-part of application No. 12/238,026, filed on Sep. 25, 2008, now Pat. No. 8,049,061, and a continuation-in-part of application No. 12/237,998, filed on Sep. 25, 2008, now Pat. No. 8,226,603.

(60) Provisional application No. 61/316,212, filed on Mar. 22, 2010.

(51) Int. Cl.
  *A61M 37/00* (2006.01)
  *A61F 2/95* (2013.01)
  *A61F 2/958* (2013.01)
  *A61L 29/16* (2006.01)
  *A61M 25/10* (2013.01)

(52) U.S. Cl.
  CPC .... *A61F 2002/9583* (2013.01); *A61M 25/104* (2013.01); *A61M 2025/105* (2013.01); *A61M 2025/1031* (2013.01); *A61M 2025/1075* (2013.01); *A61M 2025/1086* (2013.01)

(56) References Cited

U.S. PATENT DOCUMENTS

| | | |
|---|---|---|
| 4,959,074 A | 9/1990 | Halpern et al. |
| 4,990,357 A | 2/1991 | Karakelle et al. |
| 5,026,607 A | 6/1991 | Kiezulas |
| 5,049,131 A | 9/1991 | Deuss |
| 5,061,273 A | 10/1991 | Yock |
| 5,092,841 A | 3/1992 | Spears |
| 5,102,402 A | 4/1992 | Dror et al. |
| 5,272,012 A | 12/1993 | Opolski |
| 5,295,978 A | 3/1994 | Fan et al. |
| 5,304,121 A | 4/1994 | Sahatjian |
| 5,324,261 A | 6/1994 | Amundson et al. |
| 5,370,614 A | 12/1994 | Amundson et al. |
| 5,380,299 A | 1/1995 | Fearnot et al. |
| 5,456,694 A | 10/1995 | Marin et al. |
| 5,458,573 A | 10/1995 | Summers |
| 5,458,615 A | 10/1995 | Klemm et al. |
| 5,476,476 A | 12/1995 | Hillstead |
| 5,507,768 A | 4/1996 | Lau et al. |
| 5,549,551 A | 8/1996 | Peacock et al. |
| 5,562,922 A | 10/1996 | Lambert |
| 5,578,340 A | 11/1996 | Ogawa et al. |
| 5,588,962 A | 12/1996 | Nicholas et al. |
| 5,609,629 A | 3/1997 | Fearnot et al. |
| 5,620,738 A | 4/1997 | Fan et al. |
| 5,674,192 A | 10/1997 | Sahatjian et al. |
| 5,685,847 A | 11/1997 | Barry |
| 5,707,385 A | 1/1998 | Williams |
| 5,728,420 A | 3/1998 | Keogh |
| 5,733,925 A | 3/1998 | Kunz et al. |
| 5,756,144 A | 5/1998 | Wolff et al. |
| 5,766,158 A | 6/1998 | Opolski |
| 5,782,855 A | 7/1998 | Lau et al. |
| 5,820,917 A | 10/1998 | Tuch |
| 5,820,918 A | 10/1998 | Ronan et al. |
| 5,821,343 A | 10/1998 | Keogh |
| 5,824,049 A | 10/1998 | Ragheb et al. |
| 5,837,313 A | 11/1998 | Ding et al. |
| 5,843,033 A | 12/1998 | Ropiak |
| 5,843,089 A | 12/1998 | Sahatjian et al. |
| 5,848,969 A * | 12/1998 | Panescu et al. .............. 600/462 |
| 5,860,954 A | 1/1999 | Ropiak |
| 5,868,719 A | 2/1999 | Tsukernik |
| 5,891,506 A | 4/1999 | Keogh |
| 5,893,840 A | 4/1999 | Hull et al. |
| 5,900,246 A | 5/1999 | Lambert |
| 5,914,182 A | 6/1999 | Drumheller |
| 5,925,552 A | 7/1999 | Keogh et al. |
| 5,928,916 A | 7/1999 | Keogh |
| 5,945,319 A | 8/1999 | Keogh |
| 5,954,706 A | 9/1999 | Sahatjian |
| 5,977,163 A | 11/1999 | Li et al. |
| 5,980,972 A | 11/1999 | Ding |
| 5,981,568 A | 11/1999 | Kunz et al. |
| 6,010,521 A | 1/2000 | Lee et al. |
| 6,017,741 A | 1/2000 | Keogh |
| 6,033,719 A | 3/2000 | Keogh |
| 6,039,721 A | 3/2000 | Johnson et al. |
| 6,048,620 A | 4/2000 | Zhong |
| 6,050,980 A | 4/2000 | Wilson |
| 6,074,659 A | 6/2000 | Kunz et al. |
| 6,093,463 A | 7/2000 | Thakrar |
| 6,096,726 A | 8/2000 | Opolski |
| 6,099,562 A | 8/2000 | Ding et al. |
| 6,099,926 A | 8/2000 | Thakrar |
| 6,106,889 A | 8/2000 | Beavers et al. |
| 6,107,416 A | 8/2000 | Patnaik et al. |
| 6,110,590 A | 8/2000 | Zarkoob et al. |
| 6,129,705 A | 10/2000 | Grantz |
| 6,143,037 A | 11/2000 | Goldstein et al. |
| 6,146,358 A | 11/2000 | Rowe |
| 6,200,257 B1 | 3/2001 | Winkler |
| 6,214,901 B1 | 4/2001 | Chudzik et al. |
| 6,218,016 B1 | 4/2001 | Tedeschi et al. |
| 6,248,127 B1 | 6/2001 | Shah et al. |
| 6,254,921 B1 | 7/2001 | Chappa et al. |
| 6,264,633 B1 | 7/2001 | Knorig |
| 6,268,390 B1 | 7/2001 | Kunz |
| 6,270,831 B2 | 8/2001 | Kumar et al. |
| 6,280,411 B1 | 8/2001 | Lennox |
| 6,303,179 B1 | 10/2001 | Koulik et al. |
| 6,306,166 B1 | 10/2001 | Barry et al. |
| 6,306,421 B1 | 10/2001 | Kunz et al. |
| 6,335,029 B1 | 1/2002 | Kamath et al. |
| 6,364,856 B1 | 4/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,379,691 B1 | 4/2002 | Tedeschi et al. |
| 6,382,526 B1 | 5/2002 | Reneker et al. |
| 6,395,208 B1 | 5/2002 | Herweck et al. |
| 6,409,716 B1 | 6/2002 | Sahatjian et al. |
| 6,419,692 B1 | 7/2002 | Yang et al. |
| 6,443,942 B2 | 9/2002 | Van Antwerp et al. |
| 6,447,835 B1 | 9/2002 | Wang et al. |
| 6,461,666 B2 | 10/2002 | Park |
| 6,475,434 B1 | 11/2002 | Darouiche |
| 6,491,938 B2 | 12/2002 | Kunz et al. |
| 6,491,965 B1 | 12/2002 | Berry et al. |
| 6,506,408 B1 | 1/2003 | Palasis |
| 6,506,411 B2 | 1/2003 | Hunter et al. |
| 6,515,009 B1 | 2/2003 | Kunz et al. |
| 6,517,888 B1 | 2/2003 | Weber |
| 6,520,425 B1 | 2/2003 | Reneker |
| 6,521,283 B1 | 2/2003 | Yianni |
| 6,524,274 B1 | 2/2003 | Rosenthal et al. |
| 6,537,194 B1 | 3/2003 | Winkler |
| 6,544,221 B1 | 4/2003 | Kokish et al. |
| 6,544,223 B1 | 4/2003 | Kokish |
| 6,544,544 B2 | 4/2003 | Hunter et al. |
| 6,545,097 B2 | 4/2003 | Pinchuk et al. |
| 6,555,157 B1 | 4/2003 | Hossainy |
| 6,555,225 B1 | 4/2003 | Yoshioka et al. |
| 6,571,771 B2 | 6/2003 | Doering et al. |
| 6,579,539 B2 | 6/2003 | Lawson et al. |
| 6,589,546 B2 | 7/2003 | Kamath et al. |
| 6,596,699 B2 | 7/2003 | Zamora et al. |
| 6,616,650 B1 | 9/2003 | Rowe |
| 6,617,142 B2 | 9/2003 | Keogh et al. |
| 6,627,246 B2 | 9/2003 | Mehta et al. |
| 6,638,563 B2 | 10/2003 | McGee et al. |
| 6,641,611 B2 | 11/2003 | Jayaraman |
| 6,645,547 B1 | 11/2003 | Shekalim et al. |
| 6,649,030 B1 | 11/2003 | Tesar |
| 6,656,156 B2 | 12/2003 | Yang et al. |
| 6,663,881 B2 | 12/2003 | Kunz et al. |
| 6,669,980 B2 | 12/2003 | Hansen |

(56) References Cited

U.S. PATENT DOCUMENTS

| | | |
|---|---|---|
| 6,673,453 B2 | 1/2004 | Beavers et al. |
| 6,676,987 B2 | 1/2004 | Zhong et al. |
| 6,683,062 B2 | 1/2004 | Opolski |
| 6,695,809 B1 | 2/2004 | Lee |
| 6,695,992 B2 | 2/2004 | Reneker |
| 6,706,408 B2 | 3/2004 | Jelle |
| 6,713,119 B2 | 3/2004 | Hossainy et al. |
| 6,719,991 B2 | 4/2004 | Darouiche et al. |
| 6,730,349 B2 | 5/2004 | Schwarz et al. |
| 6,733,819 B2 | 5/2004 | Burkett et al. |
| 6,737,447 B1 | 5/2004 | Smith et al. |
| 6,743,462 B1 | 6/2004 | Pacetti |
| 6,743,463 B2 | 6/2004 | Weber et al. |
| 6,743,521 B2 | 6/2004 | Hubbell et al. |
| 6,753,071 B1 | 6/2004 | Pacetti |
| 6,753,454 B1 | 6/2004 | Mello et al. |
| 6,764,709 B2 | 7/2004 | Flanagan |
| 6,776,771 B2 | 8/2004 | Van Moorlegem et al. |
| 6,776,772 B1 | 8/2004 | Vrijer et al. |
| 6,793,960 B1 | 9/2004 | Michal et al. |
| 6,818,247 B1 | 11/2004 | Chen et al. |
| 6,821,479 B1 | 11/2004 | Smith et al. |
| 6,821,528 B2 | 11/2004 | Scott et al. |
| 6,828,028 B1 | 12/2004 | Fukui et al. |
| 6,830,583 B2 | 12/2004 | Shah et al. |
| 6,833,153 B1 | 12/2004 | Roorda et al. |
| 6,855,366 B2 | 2/2005 | Smith et al. |
| 6,855,770 B2 | 2/2005 | Pinchuk et al. |
| 6,861,088 B2 | 3/2005 | Weber et al. |
| 6,865,810 B2 | 3/2005 | Stinson |
| 6,884,628 B2 | 4/2005 | Hubbell et al. |
| 6,887,270 B2 | 5/2005 | Miller et al. |
| 6,887,510 B2 | 5/2005 | Villareal |
| 6,890,339 B2 | 5/2005 | Sahatjian et al. |
| 6,899,731 B2 | 5/2005 | Li et al. |
| 6,904,310 B2 | 6/2005 | Knapp et al. |
| 6,918,869 B2 | 7/2005 | Shaw et al. |
| 6,918,927 B2 | 7/2005 | Bates et al. |
| 6,919,100 B2 | 7/2005 | Narayanan |
| 6,921,811 B2 | 7/2005 | Zamora et al. |
| 6,923,996 B2 | 8/2005 | Epstein et al. |
| 6,926,919 B1 | 8/2005 | Hossainy et al. |
| 6,939,320 B2 | 9/2005 | Lennox |
| 6,953,466 B2 | 10/2005 | Palasis et al. |
| 6,954,977 B2 | 10/2005 | MaGuire et al. |
| 6,991,617 B2 | 1/2006 | Hektner et al. |
| 6,994,689 B1 | 2/2006 | Zadno-Azizi et al. |
| 7,008,667 B2 | 3/2006 | Chudzik et al. |
| 7,014,913 B2 | 3/2006 | Pacetti |
| 7,048,714 B2 | 5/2006 | Richter |
| 7,048,962 B2 | 5/2006 | Shekalim et al. |
| 7,060,051 B2 | 6/2006 | Palasis |
| 7,066,904 B2 | 6/2006 | Rosenthal et al. |
| 7,083,644 B1 | 8/2006 | Moroni |
| 7,087,135 B2 | 8/2006 | Dillon |
| 7,087,263 B2 | 8/2006 | Hossainy et al. |
| 7,105,175 B2 | 9/2006 | Schwarz |
| 7,108,684 B2 | 9/2006 | Farnan |
| 7,115,299 B2 | 10/2006 | Kokish |
| 7,122,356 B2 | 10/2006 | Keogh et al. |
| RE39,438 E | 12/2006 | Shah et al. |
| 7,163,334 B2 | 1/2007 | Chase et al. |
| 7,182,779 B2 | 2/2007 | Acosta et al. |
| 7,198,855 B2 | 4/2007 | Liebmann-Vinson et al. |
| 7,201,935 B1 | 4/2007 | Claude et al. |
| 7,208,190 B2 | 4/2007 | Verlee et al. |
| 7,220,491 B2 | 5/2007 | Rouns et al. |
| 7,226,612 B2 | 6/2007 | Sohier et al. |
| 7,241,455 B2 | 7/2007 | Richard |
| 7,241,478 B2 | 7/2007 | McNeish et al. |
| 7,258,891 B2 | 8/2007 | Pacetti et al. |
| 7,267,847 B2 | 9/2007 | Karamuk |
| 7,279,175 B2 | 10/2007 | Chen et al. |
| 7,326,433 B2 | 2/2008 | Stenzel |
| 7,335,391 B1 | 2/2008 | Pacetti |
| 7,345,053 B2 | 3/2008 | Garvey |
| 7,357,940 B2 | 4/2008 | Richard et al. |
| 7,364,585 B2 | 4/2008 | Weber |
| 7,364,768 B2 | 4/2008 | Rypacek et al. |
| 7,381,418 B2 | 6/2008 | Richard |
| 7,387,810 B2 | 6/2008 | Hossainy |
| 7,390,525 B2 | 6/2008 | Epstein et al. |
| 7,398,118 B2 | 7/2008 | Knapp et al. |
| 7,402,172 B2 | 7/2008 | Chin et al. |
| 7,402,329 B2 | 7/2008 | Pacetti et al. |
| 7,407,684 B2 | 8/2008 | Spencer et al. |
| 7,442,402 B2 | 10/2008 | Chudzik et al. |
| 7,445,792 B2 | 11/2008 | Toner et al. |
| 7,449,210 B2 | 11/2008 | Malik et al. |
| 7,455,875 B2 | 11/2008 | Weber et al. |
| 7,459,169 B2 | 12/2008 | Nilsson et al. |
| 7,462,165 B2 | 12/2008 | Ding et al. |
| 7,468,210 B1 | 12/2008 | Zamora |
| 7,470,469 B1 | 12/2008 | Michal et al. |
| 7,476,246 B2 | 1/2009 | Pathak |
| 7,482,034 B2 | 1/2009 | Boulais |
| 7,485,334 B2 | 2/2009 | Kerrigan |
| 8,049,061 B2 | 11/2011 | Ehrenreich et al. |
| 8,076,529 B2 | 12/2011 | Ehrenreich et al. |
| 8,226,603 B2 | 7/2012 | Von Oepen et al. |
| 8,500,687 B2 | 8/2013 | Ehrenreich et al. |
| 2001/0026834 A1 | 10/2001 | Chappa et al. |
| 2002/0084178 A1 | 7/2002 | Dubson et al. |
| 2003/0064965 A1 | 4/2003 | Richter |
| 2003/0065355 A1 | 4/2003 | Weber |
| 2003/0077253 A1 | 4/2003 | Palasis |
| 2003/0100829 A1 | 5/2003 | Zhong et al. |
| 2003/0104030 A1 | 6/2003 | Igaki et al. |
| 2003/0206960 A1 | 11/2003 | Iversen et al. |
| 2003/0207019 A1 | 11/2003 | Shekalim et al. |
| 2003/0207907 A1 | 11/2003 | Iversen et al. |
| 2003/0236513 A1 | 12/2003 | Schwarz et al. |
| 2003/0236514 A1 | 12/2003 | Schwarz |
| 2004/0018296 A1 | 1/2004 | Castro et al. |
| 2004/0034337 A1 | 2/2004 | Boulais et al. |
| 2004/0043068 A1 | 3/2004 | Tedeschi et al. |
| 2004/0058084 A1 | 3/2004 | Shekalim et al. |
| 2004/0073284 A1 | 4/2004 | Bates et al. |
| 2004/0087984 A1 | 5/2004 | Kupiecki et al. |
| 2004/0098089 A1 | 5/2004 | Weber |
| 2004/0098106 A1 | 5/2004 | Williams et al. |
| 2004/0106987 A1 | 6/2004 | Palasis et al. |
| 2004/0126400 A1 | 7/2004 | Iversen et al. |
| 2004/0224003 A1 | 11/2004 | Schultz |
| 2005/0015046 A1 | 1/2005 | Weber et al. |
| 2005/0025802 A1 | 2/2005 | Richard et al. |
| 2005/0025808 A1 | 2/2005 | Herrmann et al. |
| 2005/0027283 A1 | 2/2005 | Richard et al. |
| 2005/0037047 A1 | 2/2005 | Song |
| 2005/0037048 A1 | 2/2005 | Song |
| 2005/0064005 A1 | 3/2005 | Dinh et al. |
| 2005/0090891 A1 | 4/2005 | Sahatjian et al. |
| 2005/0106206 A1 | 5/2005 | Herweck et al. |
| 2005/0113687 A1 | 5/2005 | Herweck et al. |
| 2005/0163954 A1 | 7/2005 | Shaw |
| 2005/0181015 A1 | 8/2005 | Zhong |
| 2005/0182361 A1 | 8/2005 | Lennox |
| 2005/0208099 A1 | 9/2005 | Caplice et al. |
| 2005/0215722 A1 | 9/2005 | Pinchuk et al. |
| 2005/0220853 A1 | 10/2005 | Dao et al. |
| 2005/0241577 A1 | 11/2005 | Shekalim et al. |
| 2005/0271701 A1 | 12/2005 | Cottone et al. |
| 2005/0278021 A1 | 12/2005 | Bates et al. |
| 2006/0008606 A1 | 1/2006 | Horn et al. |
| 2006/0013853 A1 | 1/2006 | Richard |
| 2006/0013867 A1 | 1/2006 | Richard et al. |
| 2006/0020243 A1 | 1/2006 | Speck et al. |
| 2006/0020331 A1 | 1/2006 | Bates et al. |
| 2006/0030936 A1 | 2/2006 | Weber et al. |
| 2006/0034931 A1 | 2/2006 | Hansen |
| 2006/0043650 A1 | 3/2006 | Hossainy et al. |
| 2006/0051390 A1 | 3/2006 | Schwarz |
| 2006/0073265 A1 | 4/2006 | Teichman et al. |
| 2006/0079836 A1 | 4/2006 | Holman et al. |

(56) References Cited

U.S. PATENT DOCUMENTS

| | | |
|---|---|---|
| 2006/0083768 A1 | 4/2006 | Labrecque et al. |
| 2006/0085023 A1 | 4/2006 | Davies et al. |
| 2006/0110209 A1 | 5/2006 | Shekalim et al. |
| 2006/0122697 A1 | 6/2006 | Shanley et al. |
| 2006/0165872 A1 | 7/2006 | Chappa et al. |
| 2006/0167407 A1 | 7/2006 | Weber et al. |
| 2006/0171981 A1 | 8/2006 | Richard et al. |
| 2006/0184112 A1 | 8/2006 | Horn et al. |
| 2006/0230476 A1 | 10/2006 | Atanasoska et al. |
| 2006/0280858 A1 | 12/2006 | Kokish |
| 2007/0003599 A1 | 1/2007 | Schwarz |
| 2007/0014827 A1 | 1/2007 | Larrick et al. |
| 2007/0048351 A1 | 3/2007 | Lunn |
| 2007/0172509 A1 | 7/2007 | Nguyen et al. |
| 2007/0212386 A1 | 9/2007 | Patravale et al. |
| 2007/0212388 A1 | 9/2007 | Patravale et al. |
| 2007/0212393 A1 | 9/2007 | Patravale et al. |
| 2007/0255206 A1 | 11/2007 | Reneker et al. |
| 2007/0259017 A1 | 11/2007 | Francis |
| 2007/0298069 A1 | 12/2007 | Bucay-Couto et al. |
| 2008/0015500 A1 | 1/2008 | Herweck et al. |
| 2008/0015628 A1 | 1/2008 | Dubrul et al. |
| 2008/0021385 A1 | 1/2008 | Barry et al. |
| 2008/0027531 A1 | 1/2008 | Reneker et al. |
| 2008/0050415 A1 | 2/2008 | Atanasoska et al. |
| 2008/0050418 A1 | 2/2008 | Ranade et al. |
| 2008/0051871 A1 | 2/2008 | Tuch |
| 2008/0051881 A1 | 2/2008 | Feng et al. |
| 2008/0057102 A1 | 3/2008 | Roorda |
| 2008/0085294 A1 | 4/2008 | Freyman et al. |
| 2008/0113081 A1 | 5/2008 | Hossainy et al. |
| 2008/0118544 A1 | 5/2008 | Wang |
| 2008/0124372 A1 | 5/2008 | Hossainy et al. |
| 2008/0146489 A1 | 6/2008 | Pacetti et al. |
| 2008/0181927 A1 | 7/2008 | Zhao |
| 2008/0188825 A1 | 8/2008 | Atanasoska et al. |
| 2008/0188925 A1 | 8/2008 | Zhao |
| 2008/0195079 A1 | 8/2008 | Moore et al. |
| 2008/0200975 A1 | 8/2008 | Dubson |
| 2008/0206442 A1 | 8/2008 | Shekalim et al. |
| 2008/0234799 A1 | 9/2008 | Acosta et al. |
| 2008/0254297 A1 | 10/2008 | Edelman |
| 2008/0255508 A1 | 10/2008 | Wang |
| 2008/0255509 A1 | 10/2008 | Wang |
| 2008/0255510 A1 | 10/2008 | Wang |
| 2008/0264336 A1 | 10/2008 | Schwarz et al. |
| 2008/0274159 A1 | 11/2008 | Schultz |
| 2009/0011116 A1 | 1/2009 | Herweck et al. |
| 2009/0299450 A1 | 12/2009 | Johnson et al. |
| 2010/0076377 A1 | 3/2010 | Ehrenreich et al. |
| 2010/0076401 A1 | 3/2010 | Von Oepen et al. |

FOREIGN PATENT DOCUMENTS

| | | |
|---|---|---|
| EP | 519063 | 12/1992 |
| EP | 0 565 604 | 10/1993 |
| EP | 0 689 465 | 1/1996 |
| EP | 0 708 671 | 5/1996 |
| EP | 0 712 615 | 5/1996 |
| EP | 0 797 988 | 10/1997 |
| EP | 0 803 257 | 10/1997 |
| EP | 0 819 011 | 1/1998 |
| EP | 0 826 382 | 3/1998 |
| EP | 0 836 429 | 4/1998 |
| EP | 879595 | 11/1998 |
| EP | 920843 | 6/1999 |
| EP | 932399 | 8/1999 |
| EP | 980280 | 2/2000 |
| EP | 992252 | 4/2000 |
| EP | 1 007 135 | 6/2000 |
| EP | 1 035 871 | 9/2000 |
| EP | 1 037 677 | 9/2000 |
| EP | 1 079 872 | 3/2001 |
| EP | 1 140 273 | 10/2001 |
| EP | 1 150 622 | 11/2001 |
| EP | 1 159 974 | 12/2001 |
| EP | 1 165 157 | 1/2002 |
| EP | 1 220 694 | 7/2002 |
| EP | 1 330 273 | 7/2003 |
| EP | 1 339 440 | 9/2003 |
| EP | 1 341 565 | 9/2003 |
| EP | 1 343 544 | 9/2003 |
| EP | 1 383 551 | 1/2004 |
| EP | 1 447 098 | 8/2004 |
| EP | 1 462 127 | 9/2004 |
| EP | 1 539 266 | 6/2005 |
| EP | 1 539 267 | 6/2005 |
| EP | 1 562 669 | 8/2005 |
| EP | 1 575 642 | 9/2005 |
| EP | 1 610 856 | 1/2006 |
| EP | 1 663 345 | 6/2006 |
| EP | 1 666 070 | 6/2006 |
| EP | 1 677 849 | 7/2006 |
| EP | 1 683 520 | 7/2006 |
| EP | 1 691 856 | 8/2006 |
| EP | 1 695 697 | 8/2006 |
| EP | 1 735 042 | 12/2006 |
| EP | 1 750 782 | 2/2007 |
| EP | 1 762 255 | 3/2007 |
| EP | 1 800 702 | 6/2007 |
| EP | 1 804 893 | 7/2007 |
| EP | 1 832 301 | 9/2007 |
| EP | 1 842 567 | 10/2007 |
| EP | 1 857 127 | 11/2007 |
| EP | 1 952 789 | 8/2008 |
| WO | WO9211890 | 7/1992 |
| WO | WO9211895 | 7/1992 |
| WO | WO9211896 | 7/1992 |
| WO | WO 94/21308 | 9/1994 |
| WO | WO 95/03083 | 2/1995 |
| WO | WO 96/30064 | 10/1996 |
| WO | WO 96/39949 | 12/1996 |
| WO | WO 97/33552 | 9/1997 |
| WO | WO 98/11828 | 3/1998 |
| WO | WO9831415 | 7/1998 |
| WO | WO9908729 | 2/1999 |
| WO | WO9916500 | 4/1999 |
| WO | WO9927968 | 6/1999 |
| WO | WO9929353 | 6/1999 |
| WO | WO9959649 | 11/1999 |
| WO | WO0010552 | 3/2000 |
| WO | WO0021584 | 4/2000 |
| WO | WO0032238 | 6/2000 |
| WO | WO0032267 | 6/2000 |
| WO | WO 00/45744 | 8/2000 |
| WO | WO 00/48645 | 8/2000 |
| WO | WO 01/26702 | 4/2001 |
| WO | WO 02/22198 | 3/2002 |
| WO | WO 02/43786 | 6/2002 |
| WO | WO 02/47731 | 6/2002 |
| WO | WO 03/002267 | 1/2003 |
| WO | WO 03/008005 | 1/2003 |
| WO | WO 03/045523 | 6/2003 |
| WO | WO 03/090684 | 11/2003 |
| WO | WO 03/092741 | 11/2003 |
| WO | WO 2004/000380 | 12/2003 |
| WO | WO 2004/000381 | 12/2003 |
| WO | WO 2004/006976 | 1/2004 |
| WO | WO 2004/022124 | 3/2004 |
| WO | WO 2004/028582 | 4/2004 |
| WO | WO 2004/028587 | 4/2004 |
| WO | WO 2004/028610 | 4/2004 |
| WO | WO 2004/039445 | 5/2004 |
| WO | WO 2004/043506 | 5/2004 |
| WO | WO 2004/058320 | 7/2004 |
| WO | WO 2004/060405 | 7/2004 |
| WO | WO 2004/075943 | 9/2004 |
| WO | WO 2004/091714 | 10/2004 |
| WO | WO 2004/098671 | 11/2004 |
| WO | WO 2004/098697 | 11/2004 |
| WO | WO 2005/011766 | 2/2005 |
| WO | WO 2005/011767 | 2/2005 |
| WO | WO 2005/011768 | 2/2005 |
| WO | WO 2005/011772 | 2/2005 |

(56) References Cited

FOREIGN PATENT DOCUMENTS

| | | |
|---|---|---|
| WO | WO 2005/016399 | 2/2005 |
| WO | WO 2005/018501 | 3/2005 |
| WO | WO 2005/018606 | 3/2005 |
| WO | WO 2005/027994 | 3/2005 |
| WO | WO 2005/037339 | 4/2005 |
| WO | WO 2005/039664 | 5/2005 |
| WO | WO 2005/046747 | 5/2005 |
| WO | WO 2005/049021 | 6/2005 |
| WO | WO 2005/070008 | 8/2005 |
| WO | WO 2005/072651 | 8/2005 |
| WO | WO 2005/079335 | 9/2005 |
| WO | WO 2005/079339 | 9/2005 |
| WO | WO 2005/079754 | 9/2005 |
| WO | WO 2005/089855 | 9/2005 |
| WO | WO 2005/097066 | 10/2005 |
| WO | WO 2005/098955 | 10/2005 |
| WO | WO 2005/105171 | 11/2005 |
| WO | WO 2005/115496 | 12/2005 |
| WO | WO 2006/014604 | 2/2006 |
| WO | WO 2006/014607 | 2/2006 |
| WO | WO 2006/020274 | 2/2006 |
| WO | WO 2006/020644 | 2/2006 |
| WO | WO 2006/026587 | 3/2006 |
| WO | WO 2006/029012 | 3/2006 |
| WO | WO 2006/042260 | 4/2006 |
| WO | WO 2006/044308 | 4/2006 |
| WO | WO 2006/083628 | 8/2006 |
| WO | WO 2006/102359 | 9/2006 |
| WO | WO 2006/107359 | 10/2006 |
| WO | WO 2006/108420 | 10/2006 |
| WO | WO 2006/116014 | 11/2006 |
| WO | WO 2006/128016 | 11/2006 |
| WO | WO 2006/133118 | 12/2006 |
| WO | WO 2007/008729 | 1/2007 |
| WO | WO 2007/024500 | 3/2007 |
| WO | WO 2007/030302 | 3/2007 |
| WO | WO 2007/030669 | 3/2007 |
| WO | WO 2007/047473 | 4/2007 |
| WO | WO 2007/047662 | 4/2007 |
| WO | WO 2007/120323 | 10/2007 |
| WO | WO 2007/120897 | 10/2007 |
| WO | WO 2007/127488 | 11/2007 |
| WO | WO 2008/070996 | 6/2008 |
| WO | WO 2008/087488 | 7/2008 |
| WO | WO 2008/124310 | 10/2008 |
| WO | WO 2009/005933 | 1/2009 |
| WO | WO 2010/027998 | 3/2010 |

OTHER PUBLICATIONS

U.S. Appl. No. 12/238,627, Jun. 29, 2011 Notice of Allowance.
U.S. Appl. No. 12/238,627, Jun. 18, 2011 Terminal Disclaimer Decision.
U.S. Appl. No. 12/238,627, Jun. 15, 2011 Supplemental Amendment and Terminal Disclaimer filed.
U.S. Appl. No. 12/238,627, Apr. 8, 2011 Response to Non-Final Office Action.
U.S. Appl. No. 12/238,627, Dec. 10, 2010 Non-Final Office Action.
U.S. Appl. No. 12/238,627, Oct. 25, 2010 Amendment and Request for Continued Examination (RCE).
U.S. Appl. No. 12/238,627, Oct. 15, 2010 Advisory Action.
U.S. Appl. No. 12/238,627, Sep. 23, 2010 Response to Final Office Action.
U.S. Appl. No. 12/238,627, Jul. 23, 2010 Final Office Action.
U.S. Appl. No. 12/238,627, May 10, 2010 Response to Non-Final Office Action.
U.S. Appl. No. 12/238,627, Feb. 8, 2010 Non-Final Office Action.
U.S. Appl. No. 12/238,627, Nov. 6, 2009 Response to Restriction Requirement.
U.S. Appl. No. 12/238,627, Oct. 7, 2009 Restriction Requirement.
U.S. Appl. No. 12/237,998, Jun. 25, 2012 Issue Fee payment.
U.S. Appl. No. 12/237,998, Apr. 4, 2012 Notice of Allowance.
U.S. Appl. No. 12/237,998, Mar. 26, 2012 Response to Final Office Action.
U.S. Appl. No. 12/237,998, Feb. 29, 2012 Applicant Summary of Interview with Examiner.
U.S. Appl. No. 12/237,998, Feb. 7, 2012 Advisory Action.
U.S. Appl. No.12/237,998, Dec. 22, 2011 Response to Final Office Action.
U.S. Appl. No. 12/237,998, Oct. 26, 2011 Final Office Action.
U.S. Appl. No. 12/237,998, Aug. 22, 2011 Response to Non-Final Office Action.
U.S. Appl. No. 12/237,998, Aug. 15, 2011 Examiner interview Summary Record.
U.S. Appl. No. 12/237,998, Apr. 20, 2011 Non-Final Office Action.
U.S. Appl. No. 12/237,998, Feb. 7, 2011 Response to Non-Final Office Action.
U.S. Appl. No. 12/237,998, Nov. 17, 2010 Non-Final Office Action.
U.S. Appl. No. 12/237,998, Sep. 21, 2010 Request for Continued Examination (RCE).
U.S. Appl. No. 12/237,998, Sep. 7, 2010 Advisory Action.
U.S. Appl. No. 12/237,998, Aug. 23, 2010 Response to Final Office Action.
U.S. Appl. No. 12/237,998, Jun. 21, 2010 Final Office Action.
U.S. Appl. No. 12/237,998, Apr. 7, 2010 Examiner Interview Summary Record.
U.S. Appl. No. 12/237,998, Mar. 29, 2010 Response to Non-Final Office Action.
U.S. Appl. No. 12/237,998, Dec. 28, 2009 Non-Final Office Action.
U.S. Appl. No. 12/237,998, Oct. 14, 2009 Response to Restriction Requirement.
U.S. Appl. No. 12/237,998, Sep. 15, 2009 Restriction Requirement.
U.S. Appl. No. 12/238,026, Sep. 23, 2011 Issue Fee payment.
U.S. Appl. No. 12/238,026, Jun. 29, 2011 Notice of Allowance.
U.S. Appl. No. 12/238,026, Jun. 15, 2011 Supplemental Amendment.
U.S. Appl. No. 12/238,026, Apr. 6, 2011, Response to Non-Final Office Action.
U.S. Appl. No. 12/238,026, Jan. 7, 2011 Non-Final Office Action.
U.S. Appl. No. 12/238,026, Oct. 25, 2010 Amendment and Request for Continued Examination (RCE).
U.S. Appl. No. 12/238,026, Oct. 15, 2010 Advisory Action.
U.S. Appl. No. 12/238,026, Sep. 23, 2010 Response to Final Office Action.
U.S. Appl. No. 12/238,026, Jul. 23, 2010 Final Office Action.
U.S. Appl. No. 12/238,026, May 10, 2010 Response to Non-Final Office Action.
U.S. Appl. No. 12/238,029, Feb. 8, 2010, Non-Final Office Action.
U.S. Appl. No. 12/238,026, Nov. 6, 2009 Response to Restriction Requirement.
U.S. Appl. No. 12/238,026, Oct. 7, 2009 Restriction Requirement.
U.S. Appl. No. 13/069,020, Jul. 8, 2013 Issue Fee payment.
U.S. Appl. No. 13/069,020, Apr. 8, 2013 Notice of Allowance.
U.S. Appl. No. 13/069,020, Feb. 11, 2013 Response to Non-Final Office Action.
U.S. Appl. No. 13/069,020, Nov. 9, 2012 Non-Final Office Action.
Kesting, Robert E., "Phase Inversion Membranes," in Synthetic Polymeric Membranes, 2nd Ed., Chapter 7, pp. 237-286, 1985.
Tepe et al., "Local Delivery of Paclitaxel to Inhibit Restenosis During Angioplasty of the Leg," N. Engl. J. Med, 3.58;7, pp. 689-699, Feb. 14, 2008.
Werk et al., "Inhibition of Restenosis in Femoropopliteal Arteries Paclitaxel-Coated Versus Uncoated Balloon: Femoral Paclitaxel Randomized Pilot Trial," Circulation. 2008;118:1358-1365, Sep. 8, 2008.
International Search Report and Written Opinion for PCT/US2011/029327, dated Jun. 21, 2011.

\* cited by examiner

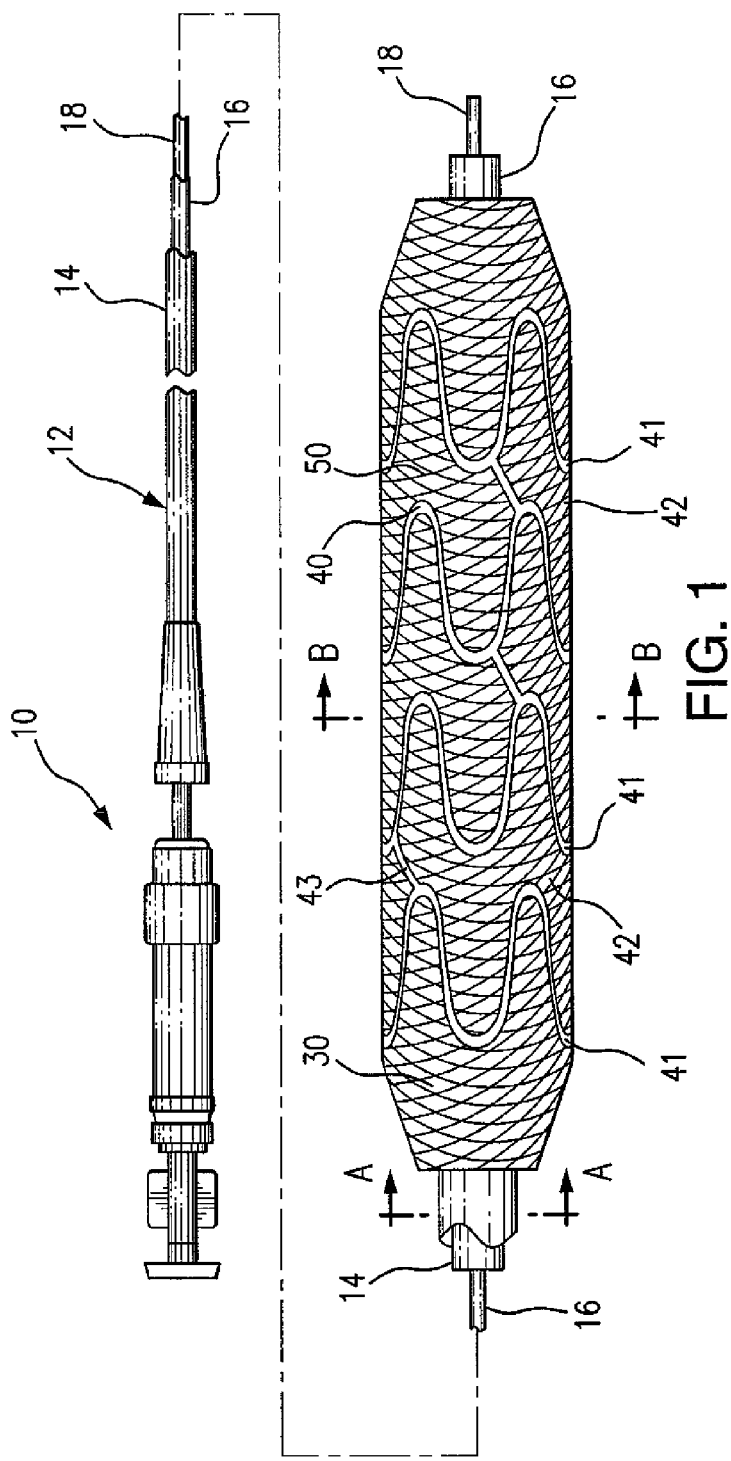
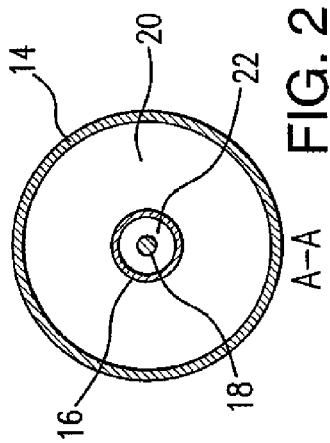

STENT DELIVERY SYSTEM HAVING A FIBROUS MATRIX COVERING WITH IMPROVED STENT RETENTION

CROSS-REFERENCE TO RELATED APPLICATIONS

This application is a divisional of U.S. patent application Ser. No. 13/069,020, filed Mar. 22, 2011, which is a continuation-in-part of U.S. patent application Ser. No. 12/238,627, filed Sep. 26, 2008, now U.S. Pat. No. 8,076,529; U.S. patent application Ser. No. 12/238,026 filed Sep. 25, 2008, now U.S. Pat. No. 8,049,061; and U.S. patent application Ser. No. 12/237,998 filed Sep. 25, 2008, now U.S. Pat. No. 8,226,603, and claims priority to U.S. Provisional Patent Application No. 61/316,212, filed Mar. 22, 2010, the disclosures of which are incorporated in their entirety by reference herein.

BACKGROUND OF THE INVENTION

Field of the Invention

The present invention generally relates to stent delivery systems. Particularly, the present invention is directed to a catheter having a fibrous matrix covering for improved stent retention, delivery and deployment.

Description of Related Art

Cardiovascular disease is prevalent in the United States and in other parts of the world. One manifestation of cardiovascular disease is atherosclerosis, which is the buildup of plaque (or fatty deposits) on the walls of blood vessels, such as coronary arteries. This buildup of plaque can grow large enough to reduce blood flow through the blood vessel. Serious damage results when an area of plaque ruptures and forms a clot, which can travel to another part of the body. If the blood vessels that feed the heart are blocked, a heart attack results. If the blood vessels to the brain are blocked, a stroke results. Thus, atherosclerosis can be fatal for some people.

Typically, atherosclerosis is treated by percutaneous transluminal coronary angioplasty (PTCA). This procedure generally entails introducing a catheter assembly into the cardiovascular system of a patient via the brachial or femoral artery, and advancing the catheter assembly through the coronary vasculature until a balloon portion thereon is positioned across an occlusive lesion. Once in position across the lesion, the balloon is inflated to a predetermined size to radially compress against the atherosclerotic plaque of the lesion to remodel the vessel wall. Subsequently, the balloon is deflated to allow the catheter assembly to be withdrawn from the vasculature.

While PCTA is widely used, it suffers from two unique problems. First, the blood vessel may suffer acute occlusion immediately after or within the initial hours after the dilation procedure. Second, the re-narrowing of an artery or other blood vessel after an initially successful angioplasty sometimes results. This blood vessel re-narrowing is commonly referred to as "restenosis," which typically occurs within the first six months after angioplasty. Restenosis is believed to be due to, among other things, the proliferation and migration of cellular components from the arterial wall, as well as through geometric changes in the arterial wall referred to as "remodeling."

To reduce the restenosis rate of angioplasty alone and to strengthen the dilated area, physicians typically implant a tubular endoprosthesis, generally called a stent, inside the vasculature at the site of the lesion or blocked segment. Stents may also be used to repair vessels having an intimal flap or dissection or to generally strengthen a weakened section of a vessel or to maintain its patency. A typical stent-delivery system for balloon expandable stents is characterized by a catheter equipped with a dilation balloon and a stent mounted on the balloon, otherwise known as a stent delivery system. In such a system, the stent is slipped over a folded catheter balloon and crimped in place. Additionally, the stent or implantable medical device may be loaded with one or more beneficial agents, such as anti-proliferative agents, for delivery to the target lesion. The stent delivery device enters the vasculature of a patient and travels through a tortuous path to the site of the lesion. The physician positions the stent across the lesion and deploys the stent so that the stent forces the plaque against the inside wall of the blood vessel (or lumen) and maintains its expanded configuration so that the patency of the blood vessel is maintained.

A concern with stent deployment, however, is possible slippage and early unintentional release of the stent. The stent may release from the balloon during delivery or deployment, such as in small or heavily occluded arteries where contact with either the arterial wall or the lesion to be treated may occur. Additionally, passage of the exposed stent through a valve may cause the stent to be dislodged from the balloon. If the stent is dislodged from or moved relative to the balloon, the system may not be able to correctly implant the stent into body lumen. The steps necessary to remove such a stent can be complicated, and may even require invasive surgery.

Different methods have been attempted to maintain the position of the stent on the expandable member. One such method involves surrounding the catheter and stent assembly with a protective sheath, which is retracted prior to inflation of the expandable member. The use of the sheath, however, increases the profile of the catheter assembly which must traverse narrow vessels. Dissolvable bands or members also have been applied to the stent surface in an effort to hold the stent in place. The bands, however, also add significantly to the outer diameter of the stent assembly and leave exposed and irregular contours of the stent assembly.

Other methods to increase stent retention include providing protrusions on the balloon or on the catheter near the balloon, the protrusions having shoulders above and/or below the stent location which bears against the stent when it is subjected to an axial force. Slight inflation of the balloon to fill cells or gaps within the stent also has been employed. However, these procedures may be difficult and time consuming, and lead to weakening of the balloon wall, an increase in the pressure required to inflate the balloon, and/or additional manufacturing steps.

Other methods include coating the exterior surface of the stent delivery device with a film-forming polymer coating, which includes a solvent. However, the solvent that is present in the coating tends to remove or redistribute any drugs that have been loaded on the stent.

Accordingly, there is a continued need for an improved method and system for improved stent retention without inhibiting balloon or catheter function.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, a stent delivery system is provided comprising a catheter shaft having a proximal end portion and a distal end portion with an expandable member provided at the distal end portion of the shaft; and a matrix of fiber elements is disposed on at least a portion of the expandable member. The expandable member has a delivery condition and a deployed condition. An expandable stent is mounted on the expandable member in the delivery condition with the matrix of fiber elements disposed therebetween. The stent includes a plurality of strut elements with interstices defined therebetween. In one embodiment, the matrix of fiber elements is a sleeve disposed over an outer surface of the expandable member. At least a portion of the sleeve can be attached to the outer surface of the expandable member. In another embodiment, at least a portion of the sleeve is attached to the catheter shaft proximate the expandable member. In another embodiment, the sleeve has a length greater than a length of the expandable member.

In accordance with another aspect of the invention, a stent delivery system is provided comprising a catheter shaft having a proximal end portion and a distal end portion, and an expandable member at the distal end portion of the shaft, wherein the expandable member is formed at least in part from a matrix of fiber elements. The expandable member has a delivery condition and a deployed condition; and an expandable stent is mounted on the expandable member in the delivery condition. The stent include a plurality of strut elements with interstices defined therebetween.

A method for securing a stent onto a stent delivery system is also provided. In one embodiment, the method comprises providing an intraluminal catheter device including a catheter shaft having a proximal end portion and a distal end portion with an expandable member disposed at the distal end portion of the shaft; and disposing a matrix of fiber elements on at least a portion of the expandable member. The expandable member has a delivery condition and a deployed condition. The method further includes providing an expandable stent having a plurality of strut elements with interstices defined therebetween, and mounting the expandable stent on the expandable member in the delivery condition with the matrix of fiber elements disposed therebetween. In one embodiment, mounting the expandable stent includes crimping the stent until the matrix protrudes outwardly into the interstices of the stent.

In another embodiment, a method for securing a stent onto a stent delivery system comprises providing an intraluminal catheter device including a catheter shaft having a proximal end portion and a distal end portion with an expandable member disposed at the distal end portion of the shaft, and providing an expandable stent having a plurality of strut elements with interstices defined therebetween. The expandable member has a delivery condition and a deployed condition, and the expandable member is formed at least in part from a matrix of fiber elements. The method further includes mounting the expandable stent on the expandable member in the delivery condition.

In one embodiment, disposing the matrix of fiber elements includes electrospinning fiber elements on the expandable member. In another embodiment, disposing the matrix of fiber elements includes forming the matrix as a sleeve and positioning the sleeve over an outer surface of the expandable member. At least a portion of the sleeve can be attached to the outer surface of the expandable member or to the catheter shaft proximate the expandable member.

Generally, the stent includes a plurality of strut elements with the interstices defined therebetween. The matrix of fiber elements preferably protrudes outwardly into the interstices of the stent. If desired, the matrix of fiber elements can protrude outwardly through the interstices beyond an outer surface of the stent, to engage an outer surface of the stent, or to engage the side surfaces facing the interstices defined between the strut elements. Additionally, or alternatively, the matrix of fiber elements is adhered to a surface of the stent. Adhering the matrix of fiber elements can be performed with solvent or with heat.

Generally, the fiber elements of the matrix of fiber elements are electrospun fibers and/or melt-blown fibers. The fiber elements include polyamides, polyurethanes, fluoropolymers, polyolefins, polyimides, polyimines, (methyl) acrylic polymers, polyesters, and co-polymers thereof. If desired, the fiber elements have a cross-sectional diameter of from about 2.5 micrometers to about 10 micrometers.

A beneficial agent can be provided on at least a portion of the expandable member, on the fiber elements of the matrix of fiber elements, and/or on at least a portion of the stent. Generally, the beneficial agent can include anti-proliferative, anti-inflammatory, antineoplastic, antiplatelet, anti-coagulant, anti-fibrin, antithrombonic, antimitotic, antibiotic, anti-allergic and antioxidant compounds and combinations thereof.

It is to be understood that both the foregoing general description and the following detailed description are exemplary and are intended to provide further explanation of the claimed invention.

The accompanying drawings, which are incorporated in and constitute part of this specification, are included to illustrate and provide a further understanding of the product and method of the invention. Together with the description, the drawings serve to explain the principles of the invention.

BRIEF DESCRIPTION OF THE DRAWINGS

FIG. 1 is a schematic view of a stent delivery catheter system in accordance with one embodiment of the invention;

FIG. 2 is a cross-sectional view taken along lines A-A in FIG. 1;

DETAILED DESCRIPTION OF THE PREFERRED EMBODIMENT

Reference will now be made in detail to the present preferred embodiments of the invention, examples of which are illustrated in the accompanying drawings. The method and corresponding steps of the invention will be described in conjunction with the detailed description of the intravascular stent delivery catheter device.

In accordance with the present invention, a stent delivery system having improved stent retention is provided. Generally, the stent delivery system includes a catheter shaft having a proximal end portion and a distal end portion with an expandable member provided at the distal end portion of the shaft; and a matrix of fiber elements is disposed on at least a portion of the expandable member. The expandable member has a delivery condition and a deployed condition. An expandable stent is mounted on the expandable member in the delivery condition with the matrix of fiber elements disposed therebetween. The matrix of fiber elements is configured to retain the stent on the expandable member while in the delivery condition and improve stent retention as catheter is delivered through the vasculature to the target treatment site.

Figure 3:
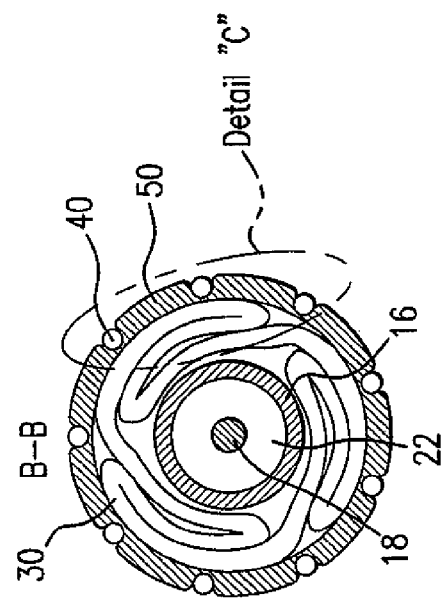
FIG. 3 is a cross-sectional view taken along lines B-B in FIG. 1.

An exemplary embodiment of the intraluminal stent delivery system is shown schematically in FIGS. 1, 2 and 3. As shown in FIGS. 1, 2 and 3, the intraluminal medical device 10 generally includes an elongated catheter shaft 12 having a proximal end and a distal end, an expandable member 30 located proximate the distal end of the catheter shaft, and a matrix of fiber elements 50 disposed on the expandable member 30. An expandable stent 40 is mounted on the expandable member 30 with the matrix of fiber elements 50 therebetween.

A variety of catheter assemblies, particularly dilatation balloon catheters, are known and suitable for the stent delivery system of the invention. The elongated catheter is sized and configured for delivery through a tortuous anatomy, preferably using a guidewire 18. For purpose of illustration and not limitation, the catheter shaft 12 embodied herein comprises an outer tubular member 14 and an inner tubular member 16. As shown in FIG. 2, the inner tubular member 16 defines the guidewire lumen 22 for the guidewire 18. Although FIGS. 1 and 2 illustrate the guidewire lumen 22 with an over-the-wire (OTW) configuration, the guidewire lumen 22 can be configured for rapid-exchange (RX) delivery, as is well known in the art. Alternatively, the catheter body can include a fixed guidewire to permit the catheter to be delivered to a vessel location without the use of a separate guidewire if desired.

In combination with the outer tubular member 14, the inner tubular member 16 also defines an inflation lumen 20 extending between the proximal end portion and the distal end portion of the catheter shaft 12. Specifically, as illustrated in FIG. 2, the coaxial relationship between the inner tubular member 16 and the outer tubular member 14 defines an annular inflation lumen 20 therebetween. The expandable member 30 is provided in fluid communication with the inflation lumen 20. The inflation lumen 20 can supply fluid under pressure to expand the expandable member 30 to a deployed condition, and if desired establish negative pressure to deflate the expandable member 30. The expandable member 30 can thus be inflated and deflated using the inflation lumen 20. Suitable materials and techniques are well known for construction of the catheter shaft.

The expandable member can be provided with a variety of configurations and constructions suitable for deployment of an expandable stent. Generally, and for purpose of illustration and not limitation, reference is made to an expandable member in the form of a balloon as is well known in the art. As embodied herein, the expandable member generally inflates to a cylindrical configuration with a central working length. The "working length" of the expandable member, or a balloon as embodied herein, is defined as the portion or length upon which the expandable stent is mounted to as described further below.

With reference to the balloon embodied herein, the expandable member can be fabricated from one or more polymers (e.g., mixture, blends or layers of polymers). For example, the polymers can include one or more thermoplastics and/or thermoset polymers. Examples of thermoplastics include polyolefins; polyamides (e.g., nylon, such as nylon 12, nylon 11, nylon 6/12, nylon 6, nylon 66); polyesters (e.g., polyethylene terephthalate (PET), polybutylene terephthalate (PUT), polyethylene naphthalate (PEN), polytrimethylene terephthalate (PTT)); polyethers; polyurethanes; polyvinyls; polyacrylics; fluoropolymers; copolymers and block copolymers thereof, such as block copolymers of polyether and polyamide (e.g., PEBAX®); and mixtures thereof. Examples of thermosets include elastomers (e.g., EPDM), epichlorohydrin, polyureas, nitrile butadiene elastomers, and silicones. Other examples of thermosets include epoxies and isocyanates. Biocompatible thermosets may also be used. Biocompatible thermosets include, for example, biodegradable polycaprolactone, poly (dimethylsiloxane) containing polyurethanes and ureas, and polysiloxanes. Ultraviolet curable polymers, such as polyimides, can also be used. Other examples of polymers that can be used to fabricate the expandable member include polyethylenes, polyethylene ionomers, polyethylene copolymers, polyetheretherketone (PEEK), thermoplastic polyester elastomers (e.g., Hytrel®)), and combinations thereof. The expandable member can include multiple layers provided, for example, by coextrusion.

The expandable member can be made using any suitable technique, such as blow molding, film molding, injection molding, and/or extrusion. For example, a polymer tube can be extruded, and can thereafter be stretched and blown to form a balloon. Methods of forming an expandable member from a tube are described, for example, in U.S. Pat. No. 6,500,148 to Pinchuk, et al.; U.S. Pat. No. 5,714,110 to Wang et al.; and U.S. Pat. No. 4,963,313 to Noddin et al., the disclosures of which are incorporated in their entirety by reference herein.

The expandable member has a delivery condition with a reduced profile, and a deployed condition with an expanded profile. As illustrated in FIG. 3 for purpose of illustration and not limitation, the delivery condition of the expandable member can be accomplished by folding the balloon to a reduced profile. The expandable member 30 can be folded using various techniques well known to those skilled in the art. The folding process can result in an expandable member with several folds, including but not limited to, two, three or four folds. By way of example, and not of limitation, certain exemplary folding processes that may be used in conjunction with the instant invention are described in U.S. Pat. No. 6,988,881 to Motsenbocker et al., which is hereby expressly incorporated by reference in its entirety. Although a small gap is illustrated between the inner surface of the expandable member 30 and the outer surface of the inner tubular member 16 in FIGS. 3 and 9 for purpose of illustration, it is understood that, when in the delivery condition, the expandable member 30 is typically collapsed down and around the inner tubular member 16 if provided. Alternatively, to accomplish the delivery condition, the balloon can be partially folded, crunched, crinkled or otherwise reduced to a low profile configuration.

Figure 11A:
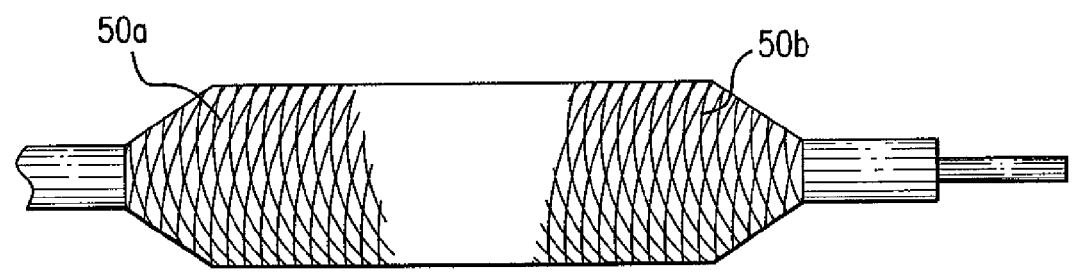
FIGS. 11a and 11b are side views schematically depicting the assembly of a stent delivery catheter system having a fibrous matrix covering in accordance with another embodiment.
Figure 11B:
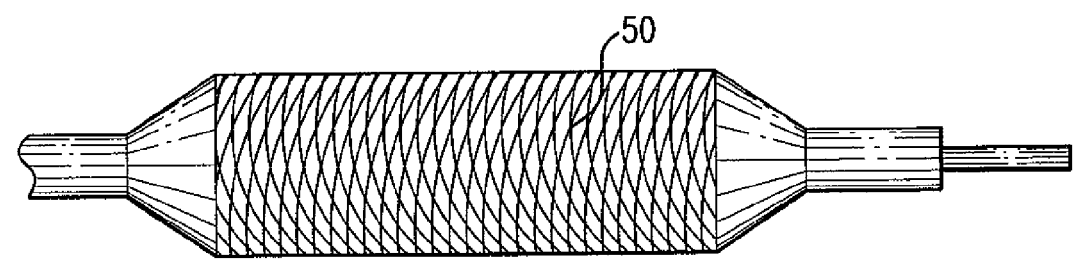

As noted above, and in accordance with one aspect of the invention, a matrix of fiber elements is disposed on at least a portion of the expandable member. For purpose of illustration and not limitation, FIG. 1 shows a fibrous matrix covering 50 over the entire length of the expandable member 30. FIG. 1 further shows the matrix of fiber elements 50 completely surrounds the expandable member 30. If desired, the matrix extends over the entire length of the expandable member, and over a portion of the catheter shaft. Alternatively, and as illustrated in FIG. 11*a*, the matrix of fiber elements can be provided over only a portion of the expandable member.

Figure 10A:
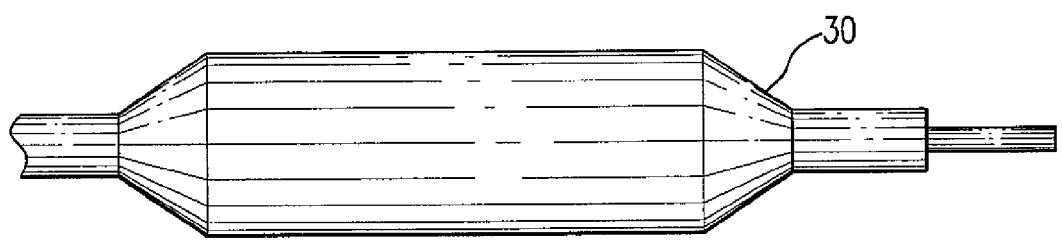
FIGS. 10a, 10b and 10c are side views schematically depicting the assembly of a stent delivery catheter system having a fibrous matrix covering formed separately as a sleeve.
Figure 10B:
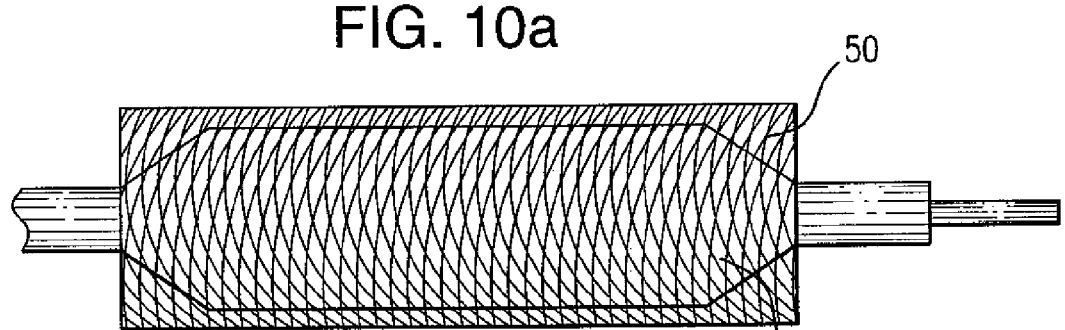
Figure 10C:
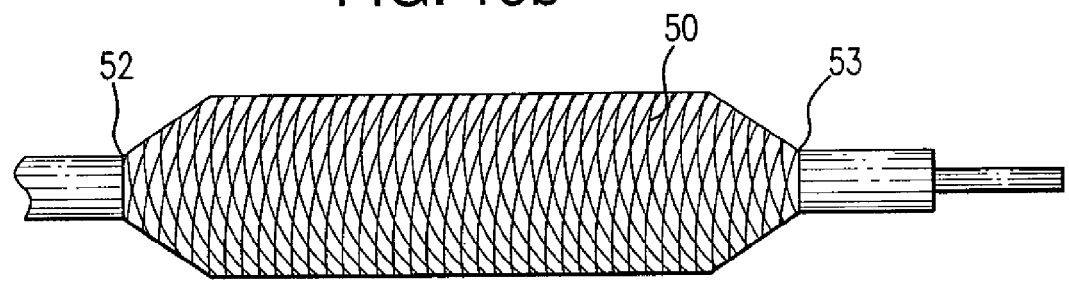

The matrix of fiber elements 50 can be formed and disposed using a variety of techniques. For example, and as illustrated in FIGS. 10*a*, 10*b*, and 10*c*, the matrix 50 can be formed separately and then over the expandable member 30. As illustrated in FIG. 10*a*, an expandable member is selected and a matrix of fiber elements 50 is then formed as a conduit or sleeve separate and apart from the fabrication of the expandable member. In accordance with one embodiment, fiber elements can be applied to a forming mandrel to form a matrix which preferably conforms in shape to that of the expandable member. The fiber elements can be applied to a forming mandrel using techniques and materials that are well known in the art. Such techniques to create a fibrous matrix include, but are not limited to, electrospinning processes and melt-blowing or spunbonding processes. In one embodiment, the mandrel diameter can be slightly larger than the diameter of the expandable member, preferably in a folded configuration, in order to permit the matrix to be slipped over the expandable member. Alternatively, however, if the fibrous matrix is constructed from a sufficiently flexible material then over-sizing of the mandrel is not necessary As illustrated in FIG. 10*b*, the fibrous matrix 50 is positioned over the expandable member. In accordance with a preferred embodiment of the invention, the expandable member is folded into a low profile configuration prior to positioning the matrix. In accordance with one embodiment of the invention and as illustrated in FIG. 10*c*, the matrix has a proximal end portion 52 and a distal end portion 53. Preferably, the matrix is adhered to the expandable member by attaching at least one of the proximal end or distal end portions of the matrix to the expandable member. Either the proximal end or distal end portions are attached to the expandable member at positions proximal and distal to the working length of the expandable member. The "working length" of the expandable member, preferably a balloon, is defined as the portion that is generally cylindrical after inflation of the expandable member. In one embodiment, the proximal end portion of the fibrous matrix 50 is attached at a position proximal to the portion of the expandable member that is generally cylindrical after expansion of the expandable member. In another embodiment, the distal end portion of the matrix is attached at a position distal to the portion of the expandable member that is generally cylindrical after expansion of the expandable member. In yet another embodiment, both the distal and proximal end portions of the matrix are attached to positions proximal and distal to the portion of the expandable member that is generally cylindrical after expansion of the expandable member. In yet another embodiment, at least one of the proximal or distal end portions of the matrix is attached to the catheter shaft. The proximal or distal end portions of the matrix are attached to the expandable member or the catheter shaft using various techniques known in the art, including but not limited to, adhesion, thermal welding, heat shrink bands and direct solvent bonding.

In accordance with one embodiment, it may be necessary to reduce the diameter of the matrix in order to create a thermal weld using a laser or another heat source as is well known in the art. Alternatively, heat shrink bands can be used at the bonding locations to attach the matrix. Another method includes using directed solvent bonding to weld the locations. The direct solvent bonding technique further reduces the profile of the matrix and enables a secure bond to be formed. In accordance with another embodiment, it is also possible to reduce the diameter of the matrix by twisting it in a candy-wrapper fashion to bring the matrix closer to positions proximal or distal to the working length of the expandable member and/or the catheter shaft and further enable a secure bond to be formed. Any combination of the methods discussed herein may be used to adhere the electrospun matrix to the surface of the expandable member.

In accordance with another embodiment of the invention, the fibrous matrix is electrospun directly onto the surface of the expandable member. The expandable portion of an intraluminal catheter is positioned beneath the nozzle of an electrospinning apparatus in order to direct an electrospun fiber toward the expandable member and catheter shaft. The catheter device is positioned adequately distant from the electrospinning nozzle to ensure that the electrospun fibers are able to dry as they travel the gap toward the catheter device. Drying of the electrospun fibers occurs through the evaporation of the solvent that the electrospun fibers are dissolved within. Additionally or alternatively, the distance between the electrospinning nozzle and the device can be shortened when the fiber is ejected toward the distal and proximal portions of the working length of the expandable member. Therefore, the solvent will not evaporate as fully before the fibers reach the device and the fibers will adhere to the surface of the expandable device as the solvent evaporates when the fiber and the surface are in contact. In accordance with the invention, a fiber matrix is electrospun over the working length of the expandable member and a portion of the device proximal and distal to the working length of the expandable member. The portion of the matrix that is disposed over the portions that are proximal and distal to the working length of the expandable member will subsequently be bonded to the device. Accordingly, it is preferred to make the distal and proximal end portions of the matrix match the profile of the expandable member as closely as possible.

Additional methods for fabricating the fibrous matrix and positioning the fibrous matrix over the expandable member are described in detail in U.S. patent application Ser. No. 12/237,998 to Von Oepen et al., the disclosure of which is incorporated herein by reference in its entirety.

The fibrous matrix is configured to enhance retention of a medical device suitable for implant as described in further detail below. For example, the implantable device can be a stent, graft, stent-graft, filter, occlusive device and the like. Furthermore, the stent or medical device is not intended to be limited to cardiovascular applications. For example and not limitation, other applications within the scope of the subject matter disclosed herein include spinal or other orthopedic implants, neurovascular or gastrointestinal implants and the like.

For purpose of illustration, reference will be made herein to the medical device implant being a stent, such as shown in FIGS. 1 and 3. Particularly, FIGS. 1 and 3 show a representative balloon expandable stent generally comprising a plurality of strut elements 41 defining interstices 42 therebetween. With reference to the stent embodied herein, the strut elements form a generally tubular body defined by a series of interconnected rings, although a wide array of various stent or other medical device configurations are known and suitable for the subject matter disclosed herein.

The stent 40 embodied herein is shown in a non-expanded configuration extending along the central, working length of the expandable member 30 and mounted on the fibrous matrix covering 50 as illustrated in FIG. 1. In operation, the catheter embodied herein is advanced to a target lesion or area of treatment in the vasculature in a conventional manner with the expandable member in a non-inflated or delivery configuration. After properly positioned within the vasculature, the expandable member is then inflated by directing inflation fluid through an inflation lumen and into the interior of the expandable member. In this manner, the expandable member 30, the fibrous matrix covering 50 and ultimately the stent 40 are expanded. The expandable member 30 is then deflated with the stent 40 implanted in the vasculature at the target site of treatment.

The stent or other medical device for delivery can be made of any suitable material, such as metal, metal alloy, or polymeric material. Exemplary materials include stainless steel, nitinol, cobalt chromium alloy, ceramics and composites, bioabsorbable polymers, biostable polymers and thermotropic liquid crystal polymers. The stent or medical device to be delivered can be fabricated by utilizing any number of methods known in the art. For example, a stent can be fabricated from a hollow or formed tube that is machined using lasers, electric discharge milling, chemical etching or other known techniques. Alternatively, the stent can be fabricated from a sheet that is rolled into a tubular member, or formed of a toroidal rings, wire or filament construction as known in the art. Examples of such fabrication techniques for purpose of illustration include U.S. Pat. No. 4,733,665 to Palmaz; U.S. Pat. No. 6,908,479 to Lau et al.; U.S. Pat. No. 6,106,548 to Roubin et al.; U.S. Pat. No. 4,580,568 to Gianturco; U.S. Pat. No. 5,755,771 to Penn et al.; and U.S. Pat. No. 6,033,434 to Borghi, the disclosures of which are incorporated in their entirety by reference herein.

In accordance with the invention, the fibrous matrix is configured to retain the stent on the expandable member. As illustrated in FIG. 3, the stent 40 is mounted on the outer surface of the fibrous matrix 50. The fibrous matrix is designed and configured such that it is compressed by the stent during the mounting and/or crimping process. Depending on the material of the fibrous matrix, its density, fiber diameter and other material characteristics, the fibrous matrix that is not compressed by the stent will fill at least one or more interstices 42 formed between the adjacent stent struts 41. This fibrous filling results in a general interference between the stent 40 and fibrous matrix 50. This interference provides a mechanical retention force on the stent when removal loads are applied. The removal loads include for example and not limitation, the vessel wall during tracking, other implanted stents during stent crossing, the diseased lesion, and any combination of loads thereof. As a result of the opposing forces provided by the fibrous matrix, the stent is less likely to dislodge when the loads are applied, thereby resulting in improved stent retention. Accordingly, the fibrous matrix covering positioned over the expandable member will improve stent retention due to interference between the stent and the fibrous matrix.

In accordance with one embodiment of the invention, as illustrated in FIG. 3, portions of the fibrous matrix protrude into the interstices formed between the adjacent stent struts. Such protrusions are in contact with the side surfaces of the stent struts, which define the interstices. In one embodiment of the invention, as illustrated in FIG. 3, the side surfaces of the stent 40 are fully encapsulated and the portions of the fibrous matrix protrude into every interstice formed between the adjacent stent. However, in an alternative embodiment, the fibrous matrix can be configured such that the matrix does not protrude fully into each interstice and/or does not protrude into every interstice formed between the adjacent stent strut (not illustrated). The characteristics of the fibrous matrix depend on several characteristics, including but not limited to, material used to form fibers, fiber diameter, thickness of the overall matrix, and the density of the fibrous matrix. Therefore, the matrix can be configured to achieve a desired configuration, as illustrated by way of example and not limitation in FIGS. 4 through 7.

Figure 5:
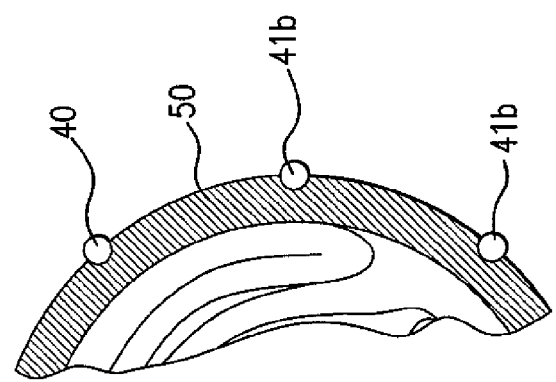
FIG. 5 is an expanded view of detail "C" in FIG. 3 in accordance with another embodiment of the invention.
Figure 7:
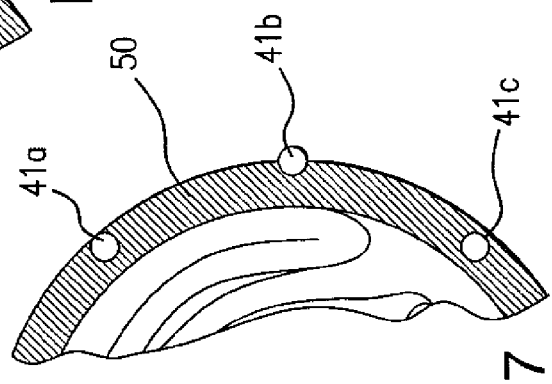
FIG. 7 is an expanded view of detail "C" in FIG. 3 in accordance with another embodiment of the invention.
Figure 4:
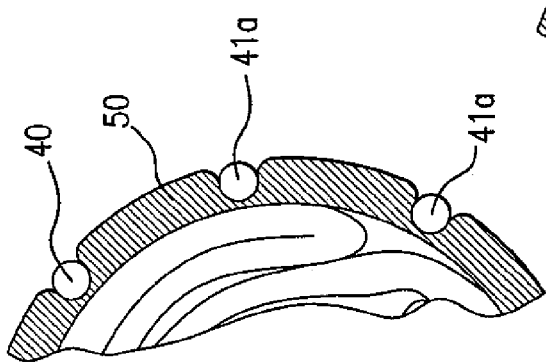
FIG. 4 is an expanded view of detail "C" in FIG. 3.
Figure 6:
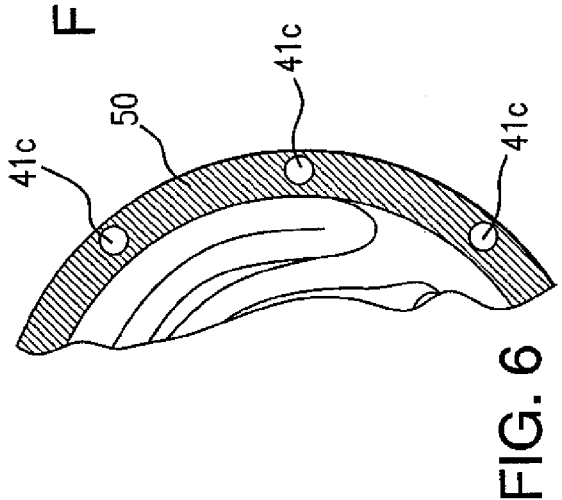
FIG. 6 is an expanded view of detail "C" in FIG. 3 in accordance with an alternative embodiment of the invention.

As illustrated in FIG. 4, the side surfaces of the stent struts are fully encapsulated and all of the portions of the covering formed of a matrix of fiber elements protruding between the adjacent stent struts have an outer diameter equal to the outer diameter of the non-expanded stent 41a. Although the stent struts are shown with circular cross-sections, it is understood that alternative cross-sections also are possible, such as square or rectangular. In accordance with another embodiment of the invention, as illustrated in FIG. 5, the portions of the matrix protruding between the adjacent stent struts have an outer diameter greater than the inner diameter of the non-expanded stent 41b. In accordance with yet another embodiment of the invention, as illustrated in FIG. 6, the portions of the matrix protruding between the adjacent stent struts have an outer diameter greater than the outer diameter of the non-expanded stent 41c. In accordance with yet another embodiment of the invention, as illustrated in FIG. 7, the portions of the matrix can have different protrusions levels with respect to the non-expanded stent. The degree of protrusion levels can be customized to achieve desired retention characteristics. For example, a large protrusion level can be used when the stent delivery device is intended for a more tortuous path and stent dislodgement is more likely.

Figure 8:
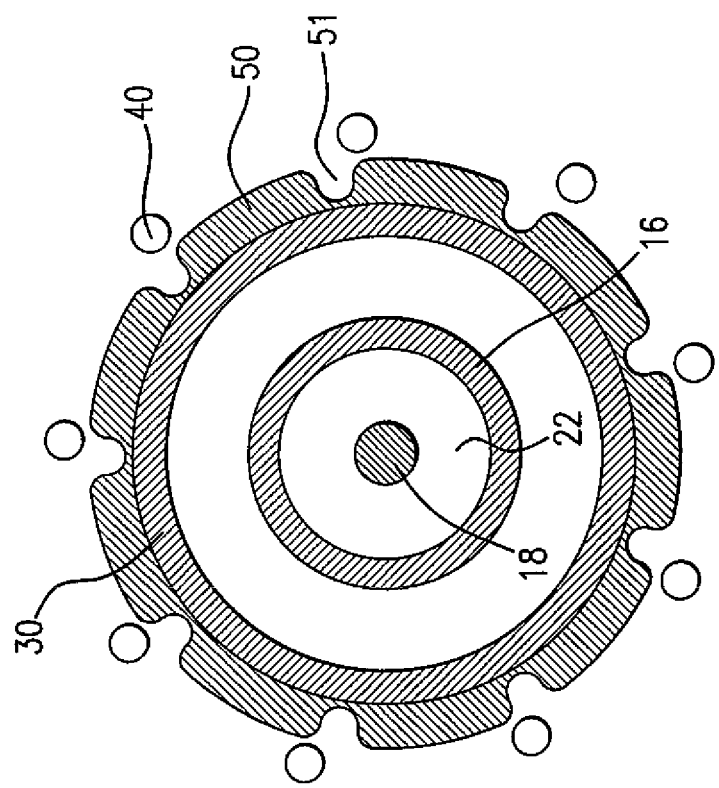
FIG. 8 is a cross-sectional view of the stent delivery catheter system of FIG. 1 in an deployed condition with the stent expanded.

The stent delivery balloon catheter of the present invention is delivered to the desired treatment site. Once the catheter is in place across the site, the expandable member is inflated in a conventional manner. As illustrated in FIG. 8, the expandable member 30 is inflated to its expanded configuration so that the stent 40 is expanded against the lumen wall. In accordance with a preferred embodiment of the invention, the fibrous matrix 50 does not disadvantageously prevent or inhibit the expandable member 30 from inflating and, at most, only minimally constrains the expandable member 30 from inflating. As the stent radially expands to the expanded configuration, as illustrated in FIG. 8, there is a degree of stent deformity as it radially expands. Therefore, the expanded stent typically has a shape that no longer matches the imprint 51 of the non-inflated stent formed in the fibrous matrix. As depicted in FIG. 8, the expanded stent is partially outside the imprint 51, with some struts 40 outside the imprint while others remain inside the imprint. However, in accordance with yet another embodiment, a stent which did not deform as it radially expanded would typically remain within the imprint 51 of the expanded configuration.

Figure 9:
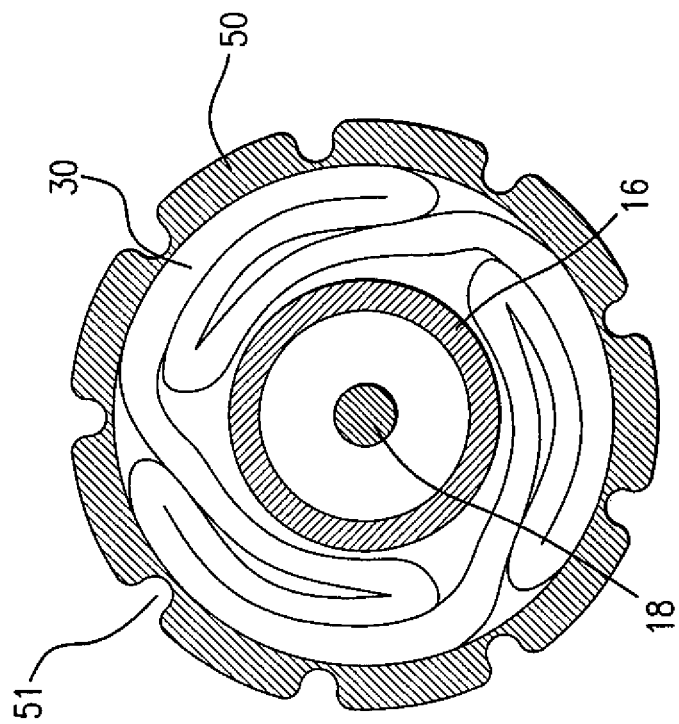
FIG. 9 is a cross-sectional view of the stent delivery catheter system of FIG. 1, with the stent removed.

Following inflation of the expandable member and expansion of the stent within the vessel, the expandable member is deflated so that it pulls away from the stent for removal. As the expandable member is deflated, the matrix is also compressed to its non-expanded state. FIG. 9 illustrates the expandable member 30 in its deflated state, with the expandable member 30 and the fibrous matrix 50 radially collapsed away from the expanded stent. As depicted in FIG. 9, and in accordance with a preferred embodiment of the invention, the imprint 51 of the stent remains clearly visible in the fibrous matrix 50. Such an imprint 51 confirms that the fibrous matrix 50 effectively protrudes into the interstices formed by the adjacent stent struts and creates a resistance fit to improve stent retention on the expandable member. In accordance with one embodiment of the invention, the fibrous matrix is kept intact and accordingly there are no fibrous elements remaining on the inner surface of the expanded stent after deployment.

In addition to the mechanical retention forces caused by the fibrous matrix, a desired amount of adhesion can be created between the fibrous matrix and the inner surface of the stent as a result of the material selected for the fibers and the solvents that are chosen in fabricating the fibers. The fibers will adhere to the inner surface of the stent while the residual solvent remains in the fibers and this adhesion will remain to some degree even after the solvent has evaporated from the matrix entirely.

It will be appreciated that in addition to the fibrous matrix characteristics such as type of polymer selected for the fibers, fiber diameter, matrix configuration, and solvents used in fiber manufacture, which can be tailored to adjust stent retention in the present invention, there are other factors that may be modified to improve the result. For example, the crimping process can be modified to include different heating steps and temperature variations to provide optimal retention of the stent.

Alternatively, post processing of the stent delivery system can be used by applying heat or solvents to further adjust the mechanical and adhesive interference between the stent and fibrous matrix sheath in order to improve the stent retention.

The fibrous matrix configuration provides for a mechanical retention force and can also provide adhesive characteristics that result in improved stent retention. Typically, the diameter of the fibers range from nano- to micro- in size, although a generally acceptable range is from 2.5 to 10 micrometers. The fiber elements are configured to achieve a desired thickness of the fibrous matrix based on the fiber size and number of layers deposited, where the desired thickness will depend upon the size and material of the medical device.

In accordance with the invention, a method is provided for securing a stent onto a stent delivery system. The method includes providing an intraluminal catheter device and positioning a fibrous matrix over at least one portion of the expandable member, as illustrated in FIG. 1. The stent, having a generally cylindrical shape, is mounted on the outer surface of the matrix. Thereafter, a radially compressive force is applied on the outer surface of the stent, thereby decreasing the outer diameter of the stent onto the fibrous matrix. The fibrous matrix is configured such that portions of the fibrous matrix protrude into the interstices formed between the adjacent stent struts.

In accordance with another embodiment, after the fibrous matrix is positioned on the expandable member and the stent is crimped thereon, an elastic sheath is placed on the outer surface of the stent and additional compressive forces are applied to the elastic sheath to collapse the stent onto the fibrous matrix. As discussed above, the crimping process may be modified to include various heating steps and temperature variations to provide optimal retention of the stent.

Figure 14:
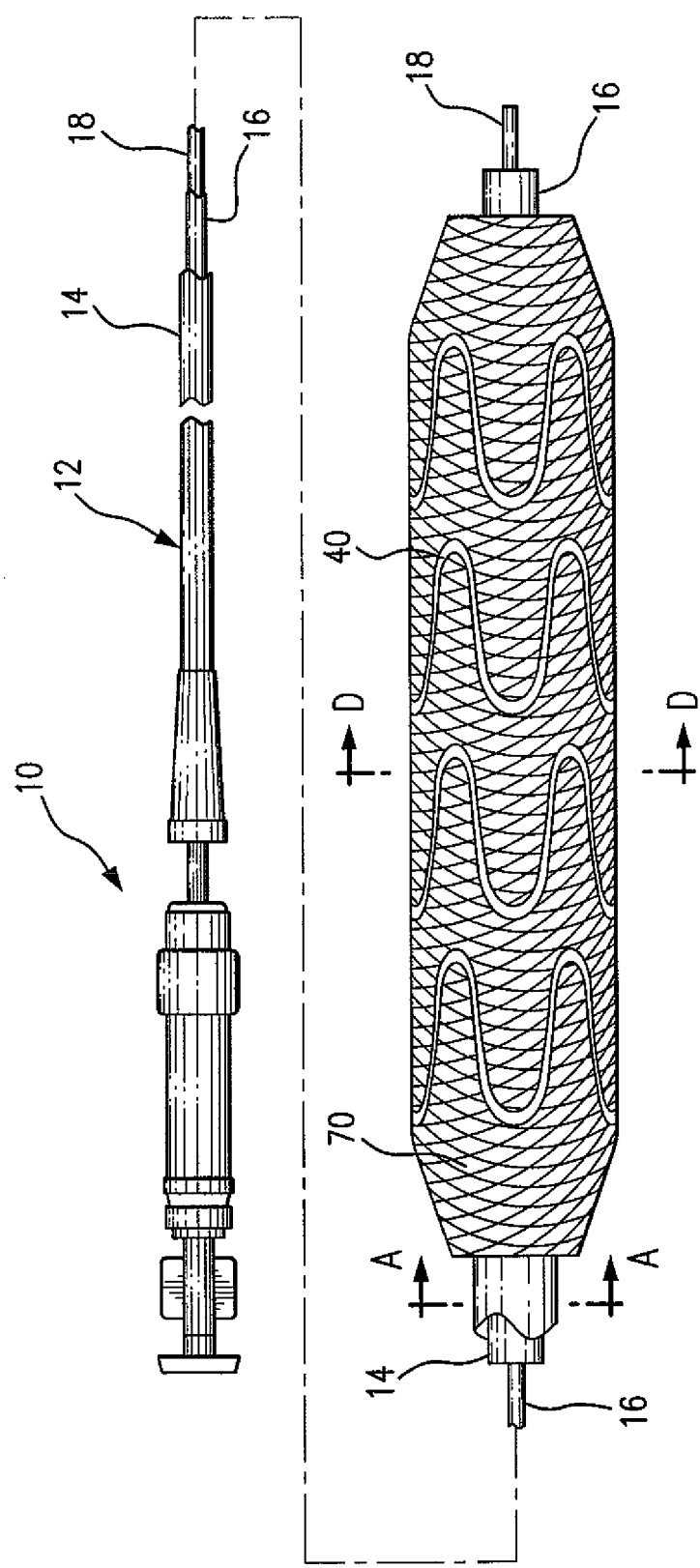
FIG. 14 is a schematic view of a stent delivery catheter system with an expandable member fabricated from a fibrous matrix and a stent engaged thereon in accordance with an alternative embodiment of the invention.
Figure 15:
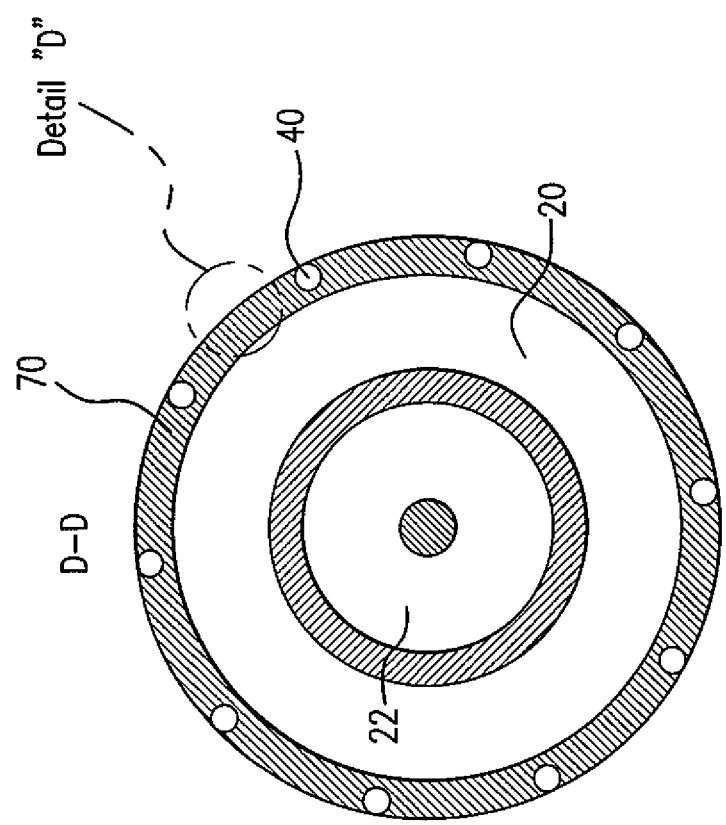
FIG. 15 is a cross-sectional view taken along lines D-D of FIG. 14.

In accordance with an alternative embodiment of the invention, as illustrated in FIGS. 14 and 15, the stent delivery system includes an elongated catheter shaft having a proximal end portion and a distal end portion and an inflation lumen disposed between the proximal end portion and distal end portion of the shaft. The stent catheter delivery system includes an expandable member disposed proximate to the distal end portion of the catheter shaft where the expandable member is formed from a matrix of fiber elements. The expandable member is formed from a fibrous matrix and is configured to be expanded from a first profile to a second profile. An expandable stent 40 having an outer surface and inner surface and a generally cylindrical shape is mounted on the outer surface of the expandable member. The stent includes a plurality of struts, each strut having an inner surface and side surfaces. The expandable member fabricated from a fibrous matrix is configured to retain the stent on the matrix.

In accordance with the invention, the expandable member fabricated from a fibrous matrix is configured to retain the stent on the expandable member. As illustrated in FIG. 15, the stent is mounted on the outer surface of expandable member formed from a fibrous matrix 70. As discussed above with respect to a fibrous matrix surrounding an expandable member, the expandable member formed from a fibrous matrix is similarly designed and configured such that it is compressed by the stent during the mounting and/or crimping process. Depending on the polymer material of the fibrous matrix used in fabricating the expandable member, its density, fiber diameter and other material characteristics, the portions of the fibrous expandable member that is not compressed by the stent will at least partially fill one or more interstices formed between the adjacent stent struts. This fibrous filling results in a general interference between the stent and fibrous expandable member. This interference provides a mechanical retention force on the stent when removal loads are applied. The removal loads include for example and not limitation, vessel wall during tracking, other implanted stents during stent crossing, the diseased lesion, and a combination thereof. As a result of the opposing forces provided by the expandable member formed from a fibrous matrix, the stent is less likely to dislodge when the loads are applied, thereby resulting in improved stent retention. Accordingly, the fibrous matrix expandable member will improve stent retention due to interference between the stent and the fibrous matrix.

As illustrated in FIG. 15, portions of the fibrous expandable member protrude into the interstices formed between the adjacent stent struts. Such protrusions are in contact with the side surfaces of the stent struts. In one embodiment of the invention, as illustrated in FIG. 15, the side surfaces of the stent are fully encapsulated and all of the portions of the fibrous matrix balloon protrude into the interstices formed between the adjacent stent. However, in an alternative embodiment, the fibrous matrix balloon can be configured such that the fibrous matrix does not protrude fully into each interstice and/or does not protrude into every interstice formed between the adjacent stent struts (not illustrated). The characteristics of the fibrous expandable member depend on several characteristics, including but not limited to, material used to form fibers, fiber diameter, thickness of the overall balloon, and the density of the fibrous matrix. Therefore, the fibrous expandable member can be configured to achieve desired protrusion levels, as discussed above with respect to a fibrous matrix and illustrated by way of example and not limitation in FIGS. 4-7. Accordingly, although FIGS. 4-7 illustrate a fibrous matrix and mounted stent, such Figures can similarly illustrate an expandable member formed from a fibrous matrix and the varying protrusion levels with the mounted stent.

Therefore, in accordance with one embodiment, the side surfaces of the stent struts are fully encapsulated and all of the portions of the expandable member formed of a matrix of fiber elements protruding between the adjacent stent struts have an outer diameter equal to the outer diameter of the non-expanded stent. In accordance with another embodiment of the invention, the portions of the fibrous expandable member protruding between the adjacent stent struts have an outer diameter greater than the inner diameter of the non-expanded stent. In accordance with yet another embodiment of the invention, the portions of the fibrous expandable member protruding between the adjacent stent struts have an outer diameter greater than the outer diameter of the non-expanded stent. In accordance with yet another embodiment of the invention, the portions of the fibrous expandable member can have varying protrusions levels with respect to the non-expanded stent. The degree of protrusion level can be customized to achieve desired retention characteristics. For example, a large protrusion level can be used when the stent delivery device is intended for a more tortuous path and stent dislodgement is more likely.

In accordance with another embodiment, the expandable member can include a liner disposed on at least one portion of the inner surface of the expandable member. Preferably the liner is non-permeable. The liner can assist in the expansion or inflation of the expandable member.

In accordance with the invention, the fibrous matrix or the fibrous expandable member is formed of a matrix of polymeric fibers. The polymeric material of the fiber include, but are not limited to, polyamides, polyurethanes, fluoropolymers, polyolefins, polyimides, polyimines, (methyl)acrylic polymers, polyesters, polyglycolide (PGA), poly(L-lactide) (PLLA), poly(D,L-lactide) (PDLLA), poly(L-lactide-co-glycolide) (PLGA), poly(D,L-lactide-co-glycolide) (PDLGA), poly(caprolactone) (PCL), polydioxanone, poly (ethylene glycol) (PEG), poly(vinyl alcohol), and suitable copolymers thereof, poly(ester amides) (PEA), and biodegradable elastomers such as biodegradable poly(ester urethanes) (PEU), polyhydroxyalkanoates such as poly(4-hydroxybutyrate) or poly(3-hydroxybutyrate), poly(1,3-trimethylene carbonate). Alternatively, the fiber can be a combination of two or more polymeric materials.

Figure 13:
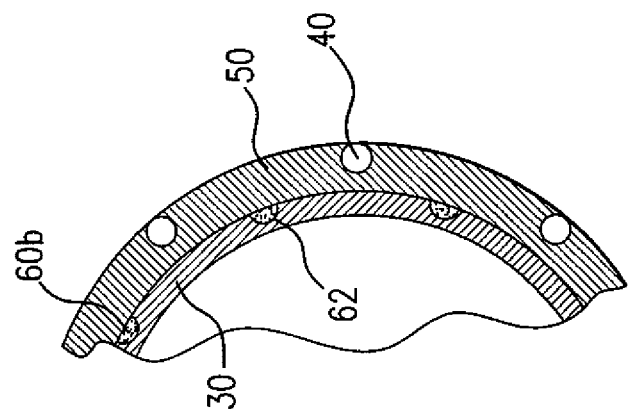
FIG. 13 is a cross-sectional detail of an alternative expandable member of FIG. 1 having a beneficial agent loaded thereon.
Figure 12:
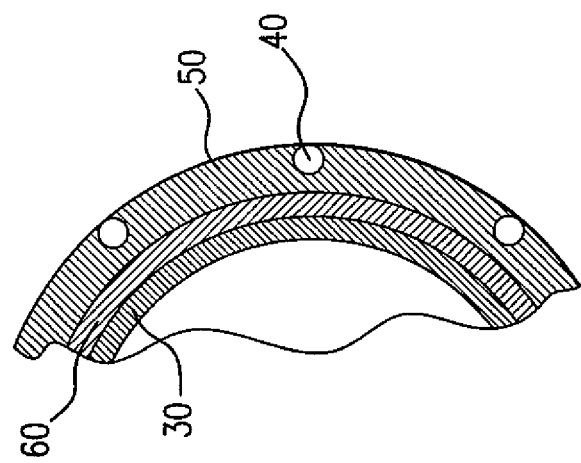
FIG. 12 is a cross-sectional detail of the expandable member of FIG. 1 having a beneficial agent loaded thereon.

In accordance with an additional embodiment, and as illustrated in FIGS. 12 and 13, the expandable member 30 can optionally have at least one beneficial agent 60 disposed on at least one portion of the outer surface of the expandable member 30. As illustrated in FIG. 12, the beneficial agent 60 can be directly applied to the surface of the expandable member 30.

Alternatively or additionally, as illustrated in FIG. 13, the outer surface of the expandable member 30 is textured to include a plurality of voids 62. The voids 62 are configured to serve as areas or locations for loading a beneficial agent 60b onto the surface of the expandable member 30. For example and not limitation, the beneficial agent coating 60 can be applied by techniques including powder coatings, spray coating, dip coating, pad printing, transfer by rolling, electrografting, and electrostatic coating, as understood in the art. The beneficial agent can be coated over a portion or the entirety of the expandable member. Accordingly, if the expandable member is textured to include a plurality of voids, then not every void is necessarily filled with beneficial agent.

In accordance with the invention, the voids are introduced during the manufacture of the expandable member. The voids are also referred to as nano- or micro-roughness. In accordance with the invention, suitable methods of creating such voids or roughness to achieve the purpose of this invention include modification of the expandable member mold and/or modification of the expandable member itself via laser machining, laser ablation, micromachining, chemical etching, electrical discharge machining (EDM), photo-etching, photolithography, electron-beam patterning, and other methods that are well known in the art for modifying the surface of a metal mold and/or a polymer. Laser types that would be useful for laser machining of the expandable member's surface include but are not limited to femto-second lasers, picosecond lasers and excimer lasers that would limit the heat affect on the material surrounding the microroughnesses. Etching can be accomplished using a suitable etchant, such as sulfuric acid on the surface of an expandable member formed from nylon. Additional methods and techniques for creating and sizing voids and loading beneficial agents therein are disclosed in U.S. patent application Ser. No. 12/237,998 to Von Oepen et al., the disclosure of which is incorporated herein by reference in its entirety.

In accordance with one embodiment, the fibrous matrix is essentially free of any beneficial agent. The method of applying the beneficial agent and positioning the fibrous matrix over the expandable member is such that the beneficial does not enter the fibrous matrix. Preferably, the matrix of fibers is relatively tightly woven to prevent the beneficial agent from entering between the fibers. Thus, if a beneficial agent is disposed on the expandable member, then the matrix of the present invention is further configured to protect the beneficial agent and prevent premature elution of the beneficial agent as the catheter device is delivered to the target site. Therefore, the stent catheter system not only is used to deploy a stent or other medical device but can also be used in connection with methods of delivering a beneficial agent. Accordingly, during stent deployment, inflation fluid is introduced through the catheter body and into the expandable member to expand or inflate the expandable member. Expansion of the expandable member causes the matrix to expand. As expansion of the fibrous matrix occurs, the tightly woven fibers will stretch and gaps between the fibers will expand in size and shape to form channels. The beneficial agent coated on the surface of the expandable member or disposed within the voids is delivered through the gaps or channels and into the vasculature or surrounding areas. In one preferred embodiment, the method of delivering beneficial agent includes diffusion of the beneficial agent from the channels in the matrix to the vessel wall when the expandable member is expanded against the vessel wall. An alternative embodiment includes a burst release technique, wherein a protective matrix is expanded or stretched as the expandable member is expanded and the beneficial agent is thereby released through the channels from the fiber matrix and into the vessel wall and surrounding area.

Figure 16:
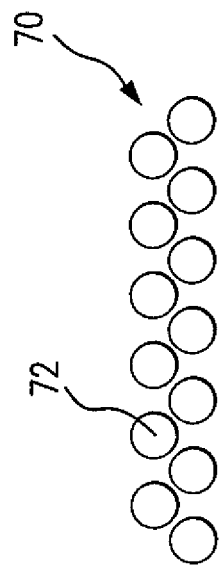
FIG. 16 is an expanded view of detail "D" in FIG. 15.
Figure 17:
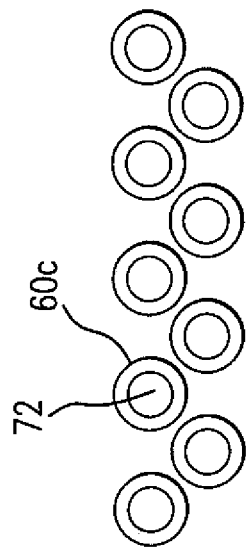
FIG. 17 is an expanded view of detail "D" in FIG. 15 in accordance with another embodiment having beneficial agent loaded thereon.

As illustrated in FIG. 16, the fibrous expandable member 70 is formed of a plurality of fibers 72. In accordance with one embodiment of the invention, the plurality of fibers 72 can also include at least one coating completely or partially surrounding the polymeric core. For example, and as shown in FIG. 17, for the purposes of illustration, the plurality of fibers 72 include a coating 60c having at least one beneficial agent. Preferably, the beneficial agent coating 60c completely surrounds the polymeric core in a co-axial configuration. In this regard, the fiber matrix not only can be used for stent retention, but can also be used to deliver a beneficial agent within a vasculature to a targeted area. The matrix and structure provided by the plurality of fibers protects the beneficial agent from eluting from the surface of the expandable member during the time required to place the device within the vessel lumen and reach the targeted area. Methods of forming an expandable member from a matrix of fiber elements and incorporating beneficial agents therein are described in U.S. patent application Ser. Nos. 12/238,026 and 12/238,627 to Ehrenreich et al., the disclosures of which are incorporated in their entirety by reference herein.

In accordance with one embodiment of the invention, the beneficial agent can further comprise at least one excipient. Excipients include but are not limited to, contrast agents, polysaccharides, amino acids, proteins, non-ionic hydrophilic polymers, ionic hydrophilic polymers, acrylates, hydrophobic polymers, aliphatic polyesters and polyester block copolymers, mucoadhesives and plasticizers, For example and not limitation, at least one beneficial agent can include anti-proliferative, anti-inflammatory, anti-neoplastic, antiplatelet, anti-coagulant, anti-fibrin, anti-thrombotic, antimitotic, antibiotic, antiallergic and antioxidant compounds. Thus, the beneficial agent can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, a retroviral vector, an anti-proliferative agent including rapamycin (sirolimus), 40-O-(2-hydroxyethyl)rapamycin (everolimus), 40-O-(3-hydroxypropyl)rapamycin, 40-O-(2-hydroxyethyoxy)ethylrapamycin, 40-O-tetrazolylrapamycin (zotarolimus, ABT-578), paclitaxel, docetaxel, methotrexate, azathioprine, vincristine, vinblastine, fluorouracil, doxorubicin hydrochloride, and mitomycin, an antiplatelet compound, an anti-coagulant, an antifibrin, an antithrombins including sodium heparin, a low molecular weight heparin, a heparinoid, hirudin, argatroban, forskolin, vapiprost, prostacyclin, a prostacyclin analogue, dextran, D-phe-pro-arg-chloromethylketone (synthetic antithrombin), dipyridamole, glycoprotein IIb/IIIa platelet membrane receptor antagonist antibody, recombinant hirudin, a thrombin inhibitor including Angiomax ä, a calcium channel blocker including nifedipine, colchicine, a fibroblast growth factor (FGF) antagonist, fish oil (omega 3-fatty acid), a histamine antagonist, lovastatin, a monoclonal antibody, nitroprusside, a phosphodiesterase inhibitor, a prostaglandin inhibitor, suramin, a serotonin blocker, a steroid, a thioprotease inhibitor, triazolopyrimidine, a nitric oxide or nitric oxide donor, a super oxide dismutase, a super oxide dismutase mimetic, estradiol, an anticancer agent, a dietary supplement including vitamins, an anti-inflammatory agent including aspirin, tacrolimus, dexamethasone and clobetasol, a cytostatic substance including angiopeptin, an angiotensin converting enzyme inhibitor including captopril, cilazapril or lisinopril, an antiallergic agent including permirolast potassium, alpha-interferon, bioactive RGD, and genetically engineered epithelial cells. Other beneficial agents which are currently available or that may be developed in the future for use with intraluminal catheter devices may likewise be used and all are within the scope of this invention.

For example and not limitation, beneficial agents effective in preventing restenosis, including those classified into the categories of anti-proliferative agents, anti-platelet agents, anti-inflammatory agents, anti-thrombotic agents, and thrombolytic agents can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, including, for example, daunorubicin, daunomycin, and plicamycin. Other sub-classes of anti-mitotic agents include anti-mitotic alkylating agents, including, for example, tauromustine, bofumustine, and fotemustine, and anti-mitotic metabolites, including, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

Any suitable process for forming a matrix of fiber elements can be used in accordance with the present invention. The matrix is a shaped structure formed from many fibers that exist in a matrix configuration. As a result of the matrix-like configuration which is tightly woven and overlapped, the matrix of fiber elements is configured to retain the stent on the matrix. Suitable processes for creating the fibrous matrix include, for example, electrospinning, melt-blowing or spunbonding.

In accordance with a preferred embodiment of the invention, the fibrous matrix or the fibrous expandable member is formed by an electrospinning process. Due to the wide variety of materials that can be used for the electrospinning process, the expandable member can be formed from a relatively soft material, which will improve deliverability of the device, and prevent damage to the anatomy during delivery. Additionally, the electrospinning process allows for the fibers to be formed with one or more coatings. In accordance with one embodiment, and as discussed above, the fibers can include a base material that supplies structure to the expandable member, and a first coating formed from one or more protective coatings. The protective coating can be dissolvable or disintegrable upon inflation of the expandable member.

In accordance with a preferred embodiment of the present invention, an exemplary method of electrospinning a matrix is provided. As discussed above and illustrated in FIGS. 10a, 10b and 10c, the exemplary process of forming a matrix includes providing a forming mandrel with a profile that is approximately the same as the desired profile of the matrix. Material fibers are then electrospun onto the mandrel surface. Alternatively, the material fibers can be electrospun directly onto the surface of the expandable member. For example, and not limitation, the electrospinning fibers are formed from polyurethane dissolved in a solvent such as acetone, tetrahydrofuran, N,N-dimethylformamide, chloroform, trifluoroethanol, hexafluoroisopropanol, or blends thereof. During the electrospinning process, the solvent begins to evaporate. When the electrospinning fibers reach the mandrel surface, the remainder of the solvent evaporates leaving the electrospun fibers. As the electrospinning layers are added, additional crossing of the electrospinning fibers will result in a dense matrix of material having radial channels or gaps passing therethrough. The size and location of these channels and gaps can be controlled through various process parameters, such as solution composition, nozzle position, and other parameters known in the art.

For example, U.S. Pat. No. 6,382,526 to Reneker et al. and U.S. Pat. No. 6,520,425 to Reneker incorporated herein by reference in their entirety, are directed to a process and apparatus for the production of nanofibers. An electrospinning fixture is provided that includes a working stage for holding the mandrel or catheter device that the electrospun material matrix will be formed on. This stage should include rotational and axial movement capabilities and the motion of the stage is to be controlled by a motor synchronized with a motor controller. The stage includes a holding fixture such as a chuck that accepts the balloon member and transmits motion thereto. The holding fixture is also connected to the negative lead of a power source, making it the cathode of the electrolytic process. The positive lead of a power source is connected to the ejection nozzle, making the nozzle the anode of the electrolytic process.

Typically, electrospinning processes require high voltage but relatively low current. In one embodiment of this invention, the power source is capable of delivering 0 to 60 kilovolts of electrical potential, but generally operates in the range of 10 to 20 kilovolts during the electrospinning process. The current that is provided by the power source is generally in the 5 to 10 microampere range. It will be appreciated that these ranges can vary depending upon the electrospinning material and process parameters. Also, it can be preferable to utilize two power sources placed in parallel or in series, depending on the goals of the process.

The nozzle is connected to a reservoir filled with electrospinning material dissolved in a solvent, and is placed in fluid communication with the reservoir by a fluid transport lumen and a pump. The electrospinning material includes thermoplastic polymeric material discussed above in connection with the material of the expandable member. Suitable organic or aqueous based electrospinning solvents, include but are not limited to, acetone, methyl ethyl ketone, cyclohexanone, dichloromethane, chloroform, trifluoroethanol, hexafluoroisopropanol, tetrahydrofuran, N,N-dimethylformamide, ethyl acetate, isopropanol, ethanol, water or blends thereof. A particular embodiment of electrospinning material includes polyurethane dissolved in tetrahydrofuran, although this can be varied widely depending upon the requirements of the invention.

The nozzle can be located in a position that creates the desired electrospinning pattern. For example, if a random matrix pattern is desirable, the nozzle exit can be located greater than about 3 mm from the expandable member surface. If a more controlled pattern is desired, the nozzle can be located within about 3 mm from the expandable member surface. The nozzle exit inner diameter will typically be in the range of from about 500 micrometer to 1.5 mm in order to achieve the desired electrospinning fiber size.

The electrospinning fiber will normally be ejected from the Taylor cone adjacent to the anode toward the cathode. The fibers will preferably have diameters in the range of from about 20 nanometers to about 10 micrometers. This size range will affect the gap size of the matrix since it will determine how much gap exists between overlapping fibers. The density of the fibers and the number of fiber layers will also affect the gap size. It is important to note that various changes to the electrospinning fibers can be made in accordance with this invention, which will affect the efficacy of the solution. For example, it is possible to electrospin a fiber that has two layers, a core (inner layer) and an outer coating (outer layer), by utilizing a specific capillary nozzle. This construction will form an electrospinning fiber that has, for example, a polyurethane core and a protective agent outer coating.

To maximize fiber bonding and minimize layer delamination within the electrospun expandable member, fabrication distance can be lowered to an appropriate value to cause fibers to lightly bond between layers due to presence of more solvent with less evaporation distance.

Further process variables such as polymer solution concentration as stated previously can also affect both morphology and fiber diameter. Increasing polymer concentration and solution viscosity while holding all other variables constant generally results in larger fiber diameter. Fiber diameters can then be varied from tens of nanometers to greater than a micron based on the parameters used. Wall thickness of the nanofiber matrix could be controlled from tens of microns up to a millimeter or greater by adjusting fabrication time from a few minutes up to an hour or more. Fabrication parameters and material composition can also be optimized for each particular catheter delivery system, to allow for the desired radial force, flexibility and recoverability.

In accordance with another embodiment, the fibrous matrix which is formed into a matrix or into an expandable member is formed from a melt-blowing or spunbonding process. The melt blowing process is well known in the art and involves extruding a fiber-forming thermoplastic polymer resin in molten form through orifices of a heated nozzle into a stream of hot gas to attenuate the molten resin as fibers which form a fiber stream, the fibers being collected on a receiver in the path of the fiber stream to form a nonwoven web. The fibrous web can then be shaped into a matrix. A method for producing a melt-blown fibrous web is described in U.S. Pat. No. 3,978,185 to Buntin et al., which is incorporated herein by reference in its entirety. The spunbonding process, equally well known in the art, is similar to the melt-blowing process, the two major differences between the two processes being i) the temperature and volume of the air used to attenuate the filaments and ii) the location where the filament draw or attenuation force is applied. A melt-blowing process uses large amounts of high-temperature air to attenuate the filaments. The air temperature is typically equal to or slightly greater than the melt temperature of the polymer. In contrast, the spunbonding process generally uses a smaller volume of air close to ambient temperature to first quench the fibers and then to attenuate the fibers. Methods for producing spunbonded webs are disclosed in U.S. Pat. No. 3,338,992 to and U.S. Pat. No. 3,341,394 to Kinney; U.S. Pat. No. 3,276,944 to Levy; U.S. Pat. No. 3,502,538 to Petersen; U.S. Pat. Nos. 3,502,763 and 3,509,009 to Hartmann; U.S. Pat. No. 3,542,615 to Dobo et al. and U.S. Pat. No. 3,692,618 to Dorschner et al., the disclosures of which are incorporated herein by reference in their entirety. Both the melt-blowing and spunbonding processes can be used to produce fibers having a diameter of about 100 nanometers. Polymers that are suitable for use in the melt-blowing and spunbonding processes which can be used to form the matrix include, but are not limited to polypropylene, polyethylene, polybutylene terephthalate, Nylon 6, Nylon 11, polycarbonate, polyurethanes, polyesters, poly(vinylidenefluoride) and poly(ester-amides).

As noted above, the fibrous matrix can be formed directly on the expandable member and formed separately and attached to the surface of the expandable member or shaft. Additionally or alternatively, the fibrous matrix can form the expandable member itself where the fibrous matrix is attached directly to the elongated catheter shaft by any conventional and suitable techniques so as to be in fluid communication with an inflation lumen. Similarly, the fibrous matrix can be folded or collapsed using known and suitable techniques for assembly, packaging, delivery and deployment as is known in the art.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. A stent delivery system comprising:
a catheter shaft having a proximal end portion, a distal end portion, and an inflation lumen extending therebetween;
a balloon provided at the distal end portion of the shaft in fluid communication with the inflation lumen, the balloon having a delivery condition and a deployed condition and formed at least in part from a matrix of fiber elements to define a continuous surface substantially free of openings when in the delivery condition; and
a stent mounted on the balloon in the delivery condition, the stent including a plurality of strut elements with interstices defined therebetween, wherein a beneficial agent is disposed on at least a portion of the surface of the stent.

2. The stent delivery system of claim 1, wherein the matrix of fiber elements protrudes outwardly into the interstices of the stent.

3. The stent delivery system of claim 2, wherein the plurality of strut elements have side surfaces facing the interstices defined therebetween, the matrix of fiber elements engaging the side surfaces.

4. The stent delivery system of claim 2, wherein the matrix of fiber elements protrudes outwardly through the interstices beyond an outer surface of the stent.

5. The stent delivery system of claim 4, wherein the matrix of fiber elements protrudes outwardly through the interstices to engage an outer surface of the stent.

6. The stent delivery system of claim 1, wherein the matrix of fiber elements is adhered to a surface of the stent.

7. The stent delivery system of claim 1, wherein the fiber elements of the matrix of fiber elements are electrospun fibers.

8. The stent delivery system of claim 1, wherein the fiber elements of the matrix of fiber elements are melt-blown fibers.

9. The stent delivery system of claim 1, wherein the fiber elements of the matrix of fiber elements comprise a polymer selected from the group consisting of polyamides, polyurethanes, fluoropolymers, polyolefins, polyimides, polyimines, (methyl)acrylic polymers, polyesters, and co-polymers thereof.

10. The stent delivery system of claim 1, wherein the fiber elements of the matrix of fiber elements have a cross-sectional diameter of from about 2.5 micrometers to about 10 micrometers.

11. The stent delivery system of claim 1, wherein a beneficial agent is disposed on at least one portion of the balloon.

12. The stent delivery system of claim 11, wherein the beneficial agent is selected from the group consisting of anti-proliferative, anti-inflammatory, antineoplastic, anti-platelet, anti-coagulant, anti-fibrin, antithrombonic, antimitotic, antibiotic, antiallergic and antioxidant compounds and combinations thereof.

13. The stent delivery system of claim 1, wherein the balloon is formed from a plurality of fibers including a polymeric core and a coating at least partially surrounding the polymeric core, and further wherein the coating comprises a beneficial agent.

14. The stent delivery system of claim 13, wherein the beneficial agent is selected from the group consisting of anti-proliferative, anti-inflammatory, antineoplastic, anti-platelet, anti-coagulant, anti-fibrin, antithrombonic, antimitotic, antibiotic, antiallergic and antioxidant compounds and combinations thereof.

15. The stent delivery system of claim 1, wherein the beneficial agent is selected from the group consisting of anti-proliferative, anti-inflammatory, antineoplastic, anti-platelet, anti-coagulant, anti-fibrin, antithrombonic, antimitotic, antibiotic, antiallergic and antioxidant compounds and combinations thereof.

* * * * *